US012642677B2

(12) United States Patent
　　DiTullio

(10) Patent No.: US 12,642,677 B2
(45) Date of Patent: Jun. 2, 2026

(54) IPSILATERAL HYPOGASTRIC STENT GRAFT DELIVERY SYSTEM

(71) Applicant: Medtronic Vacular, Inc., Santa Rosa, CA (US)

(72) Inventor: Raymond Joseph DiTullio, San Rafael, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 978 days.

(21) Appl. No.: 17/877,472

(22) Filed: Jul. 29, 2022

(65) Prior Publication Data

US 2024/0033114 A1 Feb. 1, 2024

(51) Int. Cl.
　　 *A61F 2/954* (2013.01)
　　 *A61F 2/07* (2013.01)
　　 *A61F 2/958* (2013.01)

(52) U.S. Cl.
　　 CPC ............... *A61F 2/954* (2013.01); *A61F 2/07* (2013.01); *A61F 2/958* (2013.01)

(58) Field of Classification Search
　　 CPC ........... A61F 2/07; A61F 2/954; A61F 2/958; A61M 25/1011; A61M 2025/1045
　　 See application file for complete search history.

(56) References Cited

U.S. PATENT DOCUMENTS

| | | |
|---|---|---|
| 5,653,743 A | 8/1997 | Martin |
| 6,099,558 A | 8/2000 | White |
| 6,129,738 A | 10/2000 | Lashinski et al. |
| 6,251,133 B1 | 6/2001 | Richter et al. |
| 7,300,460 B2 | 11/2007 | Levine et al. |
| 8,062,345 B2 | 11/2011 | Ouellette et al. |
| 8,118,862 B2 | 2/2012 | Saeed |
| 8,474,120 B2 | 7/2013 | Hagaman et al. |
| 9,301,864 B2 | 4/2016 | Kao |
| 9,788,982 B2 | 10/2017 | Hartley et al. |
| 10,143,576 B2 | 12/2018 | Greenberg et al. |
| 10,512,533 B1 | 12/2019 | Power |
| 10,695,179 B2 | 6/2020 | Alon |
| 10,806,563 B2 | 10/2020 | Roeder et al. |
| 11,007,075 B2 | 5/2021 | Bagaoisan et al. |
| 11,020,256 B2 | 6/2021 | Syed |
| 11,096,810 B2 | 8/2021 | Roeder |
| 11,129,737 B2 | 9/2021 | Chu et al. |
| 2002/0198585 A1 | 12/2002 | Wisselink |
| 2004/0098084 A1 * | 5/2004 | Hartley .................. A61F 2/954 623/1.11 |

(Continued)

*Primary Examiner* — Sarah W Aleman
(74) *Attorney, Agent, or Firm* — Medler Ferro Woodhouse & Mills PLLC

(57) ABSTRACT

A delivery system includes a shaft including first and second main lumens spaced from each other and forming a common U-shaped lumen at distal portions of the lumens, a delivery device including a first and second members disposed within the first and second main lumens and a manifold coupling the first and second members disposed in the common U-turn lumen, wherein proximal movement of the first member of the delivery device along a first longitudinal axis causes corresponding proximal movement of the manifold within the common U-turn lumen and corresponding proximal movement of the second member along a second longitudinal axis different than the first longitudinal axis.

11 Claims, 39 Drawing Sheets

(56) References Cited

U.S. PATENT DOCUMENTS

| | | | |
|---|---|---|---|
| 2004/0243221 A1* | 12/2004 | Fawzi | A61F 2/07 |
| | | | 623/1.36 |
| 2007/0299495 A1* | 12/2007 | Zukowski | A61F 2/954 |
| | | | 623/1.11 |
| 2007/0299498 A1* | 12/2007 | Perez | A61F 2/954 |
| | | | 623/1.11 |
| 2012/0053671 A1 | 3/2012 | Mchugo et al. | |
| 2013/0131777 A1 | 5/2013 | Hartley et al. | |
| 2013/0289693 A1 | 10/2013 | Maggard et al. | |
| 2014/0180385 A1 | 6/2014 | Majercak et al. | |
| 2014/0324150 A1* | 10/2014 | Stephens | A61F 2/07 |
| | | | 623/1.11 |
| 2016/0324670 A1 | 11/2016 | Yamaguchi | |
| 2018/0177622 A1* | 6/2018 | Chu | A61F 2/06 |
| 2018/0256332 A1 | 9/2018 | Gloss et al. | |
| 2021/0393423 A1 | 12/2021 | Dorn | |

* cited by examiner

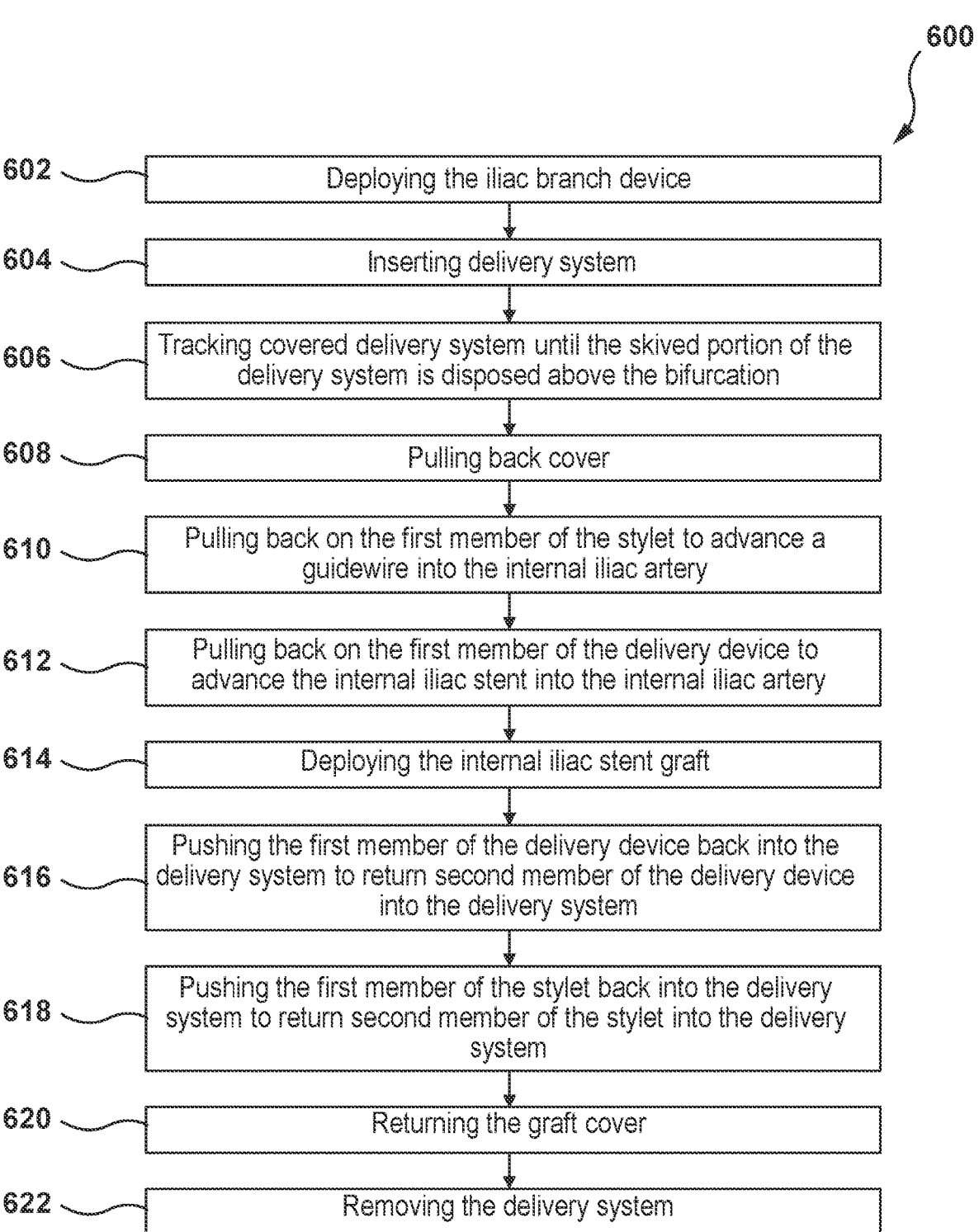

602 — Deploying the iliac branch device

604 — Inserting delivery system

606 — Tracking covered delivery system until the skived portion of the delivery system is disposed above the bifurcation 608 — Pulling back cover 610 — Pulling back on the first member of the stylet to advance a guidewire into the internal iliac artery 612 — Pulling back on the first member of the delivery device to advance the internal iliac stent into the internal iliac artery 614 — Deploying the internal iliac stent graft 616 — Pushing the first member of the delivery device back into the delivery system to return second member of the delivery device into the delivery system 618 — Pushing the first member of the stylet back into the delivery system to return second member of the stylet into the delivery system 620 — Returning the graft cover 622 — Removing the delivery system

FIG. 10

IPSILATERAL HYPOGASTRIC STENT GRAFT DELIVERY SYSTEM

FIELD OF THE INVENTION

The present invention generally relates to endovascular devices and methods, for example, devices for treatment of a diseased artery.

BACKGROUND

An aneurysm is an excessive localized enlargement of an artery caused by a weakening of the artery wall. Treatment options for aneurysms vary depending on the location, size and condition of the aneurysm. A common treatment method involves deploying a stent graft within the diseased artery to direct blood flow through the aneurysm and protecting the artery wall to prevent the aneurysm from bursting. A conventional stent-graft typically includes a radially expandable reinforcement structure, e.g., formed from a stent or a plurality of annular stent rings, and a cylindrically shaped layer of graft material defining a lumen to which the stent/stent rings are coupled.

Aneurysms may extend into the iliac arteries (also referred to as the common iliac arteries), which branch from the aorta. Each common iliac artery branches into an external iliac artery and an internal iliac artery, also referred to as the hypogastric artery. Procedures currently used to gain access to the internal iliac/hypogastric artery use a contra femoral approach by either going up and over the bifurcation via an externalized ipsi-contra through wire, using a contra femoral approach with a steerable guide catheter, or using an arm approach to come down from the top. There are many challenges with a contra approach to gaining access to the hypogastric artery and developing a stent graft due to various angulations and diameters of the anatomy. Up and over approaches can also have negative consequences to an iliac branch device, such as displacing it during the procedure which has potential accuracy concerns that could lead to patency, joint strength, and endoleaks. Strokes are a primary concern in arm access approaches.

To maintain perfusion to the hypogastric arteries, or when treating an abdominal aortic aneurysm (AAA) or iliac aneurysm, an iliac branch stent graft can be used along with a hypogastric branch stent graft to exclude the aneurysm and maintain flow into the hypogastric artery.

BRIEF SUMMARY OF THE INVENTION

In accordance with a first example hereof, a delivery system comprises a shaft and a delivery device, The shaft includes a guidewire lumen, first main lumen, a second main lumen, wherein proximal portion of the first main lumen and the second main lumen are separated, and wherein distal portions of the first main lumen and the second main lumen form a common U-turn lumen. The delivery device includes a first member disposed within the first main lumen of the shaft, a second member disposed within the second main lumen of the shaft, and a manifold coupling the first member and the second member, wherein the manifold is disposed within the common U-turn lumen of the shaft. Proximal movement of the first member of the delivery device along a first longitudinal axis causes corresponding proximal movement of the manifold within the common U-turn lumen and corresponding proximal movement of the second member along a second longitudinal axis different from the first longitudinal axis.

In a second example, in the delivery system of the first example, the delivery device further includes a balloon coupled to the second member.

In a third example, in the delivery system of the second example, the first member includes a first central lumen and a first inflation lumen, the second member includes a second central lumen and a second inflation lumen, and the manifold fluidly couples the first inflation lumen and the second inflation lumen.

In a fourth example, the delivery system of the third example further comprises a stylet including a first wire member disposed within the first main lumen of the delivery device, a second wire member disposed within the second main lumen of the delivery device, and a connector connecting distal ends of the first wire member and the second wire member, the connector being disposed within the common U-turn lumen of the shaft, wherein proximal movement of the first wire member causes corresponding proximal movement of the connector within the common U-turn lumen and corresponding proximal movement of the second wire member.

In a fifth example, the delivery system of any one of the first through fourth examples further comprises a skived portion of the shaft, wherein the skived portion of the shaft exposes a portion of the second main lumen of the shaft.

In a sixth example, the delivery system of the fifth example further comprises a cover extending from a proximal end of the delivery system to a distal portion of the delivery system, wherein the cover is movable relative to the shaft to cover and uncover the skived portion of the shaft.

In a seventh example, in the delivery system of the sixth example, the cover is longitudinally translatable to cover and uncover the skived portion of the shaft.

In an eighth example, the delivery system of any one of the first through seventh examples further comprises a distal tip coupled to a distal end of the shaft, wherein the distal tip includes a tip guidewire lumen in communication with the guidewire lumen of the shaft.

In a ninth example, in the delivery system of the fourth example, the manifold of the delivery device includes a first lumen with the first member fixedly coupled therein, and second lumen with the second member fixedly coupled therein, and an opening between the first lumen and the second lumen.

In a tenth example, in the delivery system of the ninth example, the first member includes a first opening aligned with the first inflation lumen and the opening of the manifold and the second member includes a second opening aligned with the second inflation lumen of the opening, wherein inflation fluid injected into the first inflation lumen is configured to move distally within the first inflation lumen, exit the first inflation lumen via the first opening, move through the opening in the manifold and into the second inflation lumen through the second opening, and move proximally through the second inflation lumen to the balloon of the delivery device.

In an eleventh example, in the delivery system of the ninth example, the first wire member of the stylet extends through the first lumen of the manifold and the second wire member of the stylet extends through the second lumen of the manifold.

In a twelfth example, a method of delivering and deploying a stent graft into a first branch vessel of a bifurcated vessel having a common vessel and a bifurcation bifurcating the common vessel into the first branch vessel and a second branch vessel comprises: advancing a delivery system into the second branch vessel of the bifurcated vessel such that a distal portion of the delivery system advances past the bifurcation and into the common vessel; retracting a first member of a delivery device of the delivery system proximally such that the first member retracts proximally within the second branch vessel and a second member of the delivery device spaced from the first member is moved proximally and into the first branch vessel; and deploying a stent graft from the second member of the delivery device in the first branch vessel.

In a thirteenth example, the method of the twelfth example further comprises retracting a first wire member of a stylet of the delivery device proximally such that the first wire member retracts proximally within the second branch vessel and a second wire member of the stylet spaced from the first wire member is moved proximally and into the first branch vessel.

In a fourteenth example, the method of the thirteenth example further comprises proximally retracting a cover of the delivery system to expose a skived portion of a shaft of the delivery system, wherein the during the advancing step the first member and the first wire member are disposed in a lumen of the shaft, wherein the skived portion of the shaft exposes a portion of the lumen of the shaft, and wherein retracting the cover to expose the skived portion enables the first wire member and the first member to exit the lumen of the shaft via the skived portion.

In a fifteenth example, in the method of the twelfth example, deploying the stent graft comprises inflating a balloon coupled to the second member of the delivery device to radially expand the stent graft disposed on the balloon.

In a sixteenth example, in the method of the fifteenth example, inflating the balloon comprises injecting inflation fluid into a first inflation lumen of the first member such that the inflation fluid moves distally within the first inflation lumen, the inflation fluid moves to a second inflation lumen of the second member, and the inflation fluid moves proximally within the second inflation lumen to the balloon.

In a seventeenth example, in the method of the sixteenth example, the inflation fluid moves to the second inflation lumen through a manifold of the delivery device, the manifold coupling the first member and the second member.

In an eighteenth example, in the method of the seventeenth example, the inflation fluid injection into the first inflation lumen moves distally within the first inflation lumen, exits the first inflation lumen via a first opening in the first member, through an opening in the manifold aligned with the first opening, and enters the second inflation lumen through a second opening in the second member aligned with the opening.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The foregoing and other features and advantages of the present disclosure will be apparent from the following description of embodiments hereof as illustrated in the accompanying drawings. The accompanying drawings, which are incorporated herein and form a part of the specification, further serve to explain the principles of the present disclosure and to enable a person skilled in the pertinent art to make and use the embodiments of the present disclosure. The drawings may not be to scale.

FIG. 10 is a block diagram that shows a method of using the delivery system according to embodiments hereof.

DETAILED DESCRIPTION

Figures 1A, 1B:
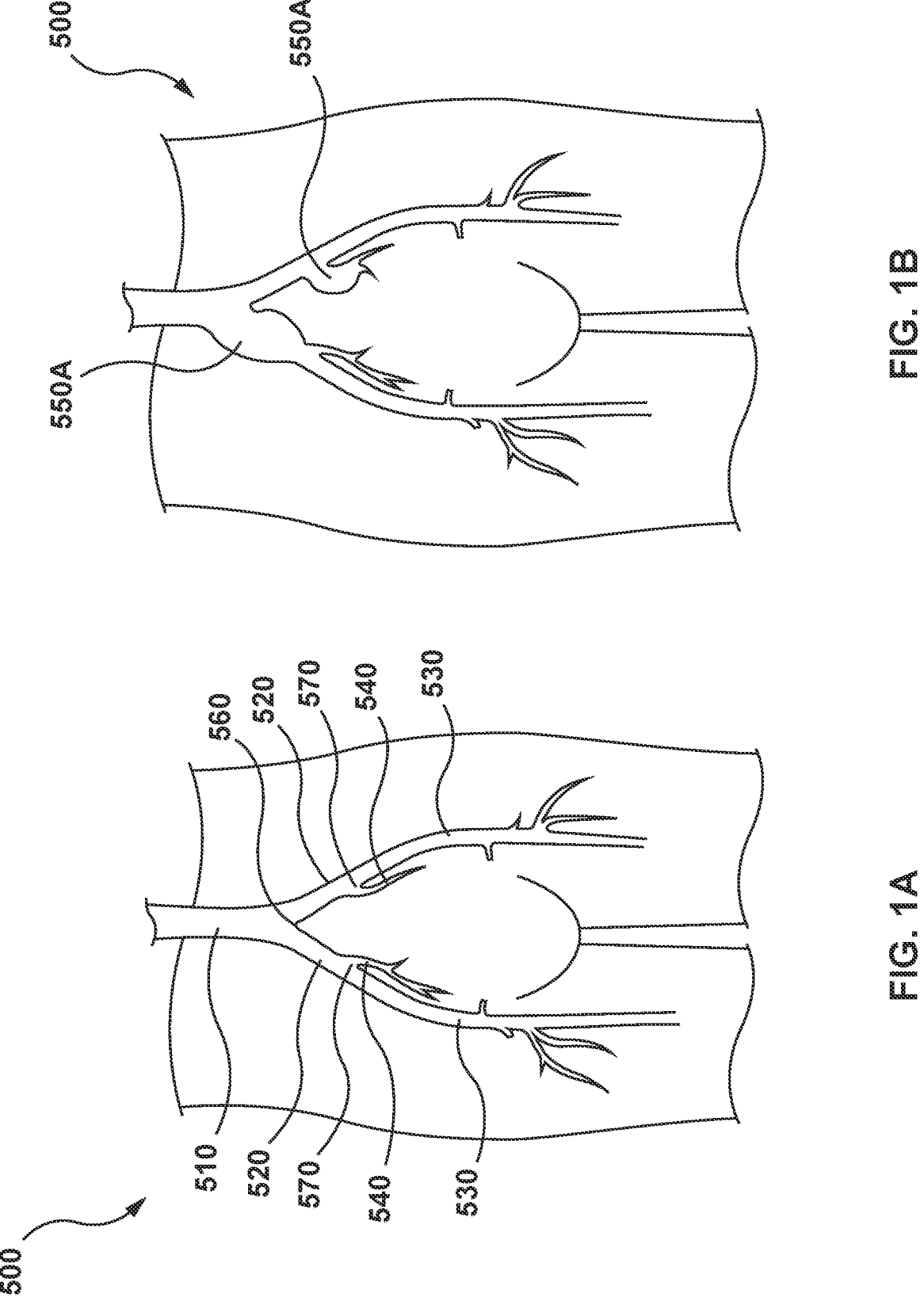
FIG. 1A shows an idealized example of a patient's vasculature according to an embodiment hereof.
FIG. 1B shows the patient's vasculature of FIG. 1A including an exemplary common iliac aneurysm and an exemplary internal iliac aneurysm according to an embodiment hereof.

It should be understood that various embodiments disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single device or component for purposes of clarity, it should be understood that the techniques of this disclosure may be performed by a combination of devices or components associated with, for example, a delivery system.

The following detailed description is merely exemplary in nature and is not intended to limit the invention of the application and uses of the invention. Furthermore, there is no intention to be bound by any expressed or implied theory presented in the preceding field of the invention, background, summary or the following detailed description.

As used in this specification, the singular forms "a", "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%. It should be understood that use of the term "about" also includes the specifically recited number of value.

The terms "proximal" and "distal" herein when used with respect to a delivery system are used with reference to the clinician using the devices. Therefore, "proximal" and "proximally" mean in the direction toward the clinician, and "distal" and "distally" mean in the direction away from the clinician. The terms "proximal" and "distal" herein when used with respect to a medical device to be implanted, such as a stent graft, are used with reference to the direction of blood flow. Therefore, "proximal" and "proximally" mean in an upstream direction, and "distal" and "distally" mean in a downstream direction.

As used herein, the term "generally" and "substantially" mean approximately. When used to describe angles such as "substantially parallel" or "substantially perpendicular" the term "substantially" means within 10 degrees of the angle. When used to describe shapes such as "substantially" or "generally" cylindrical or "substantially" or "generally" tube-shaped or "generally" or "substantially" conical, the terms mean that the shape would appear cylindrical or tube-shaped or conical to a person of ordinary skill in the art viewing the shape with a naked eye.

FIGS. 1A-1B illustrate an idealized example of a patient's vasculature 500 that may be treated with a delivery system described below according to embodiments herein. The vasculature 500 includes an aorta 510 that runs vertically along the trunk or body of the patient. The aorta 510 splits at a first bifurcation 560, located in an abdominal region of the patient, into two common iliac arteries 520 that run down each of the patient's legs. Each common iliac artery 520 splits into an external iliac artery 530 and an internal iliac artery 540 at a second bifurcation 570, as shown in FIG. 1A. The internal iliac artery 540 is the smaller terminal branch of the common iliac artery 520. As noted above, the internal iliac artery is also referred to as the hypogastric artery. The internal iliac arteries 540 supply blood to the majority of the pelvis and the structures therewithin, while the external iliac arteries 530 continue down the leg to supply blood to the lower extremities. FIG. 1B shows an exemplary common iliac aneurysm 550A and an exemplary internal iliac aneurysm 550B within the vasculature 500 of the patient. The common iliac aneurysm 550A can develop within the common iliac arteries 520 and the internal iliac aneurysm 550B can develop within the internal iliac arteries 540 of the vasculature 500.

Figure 2:
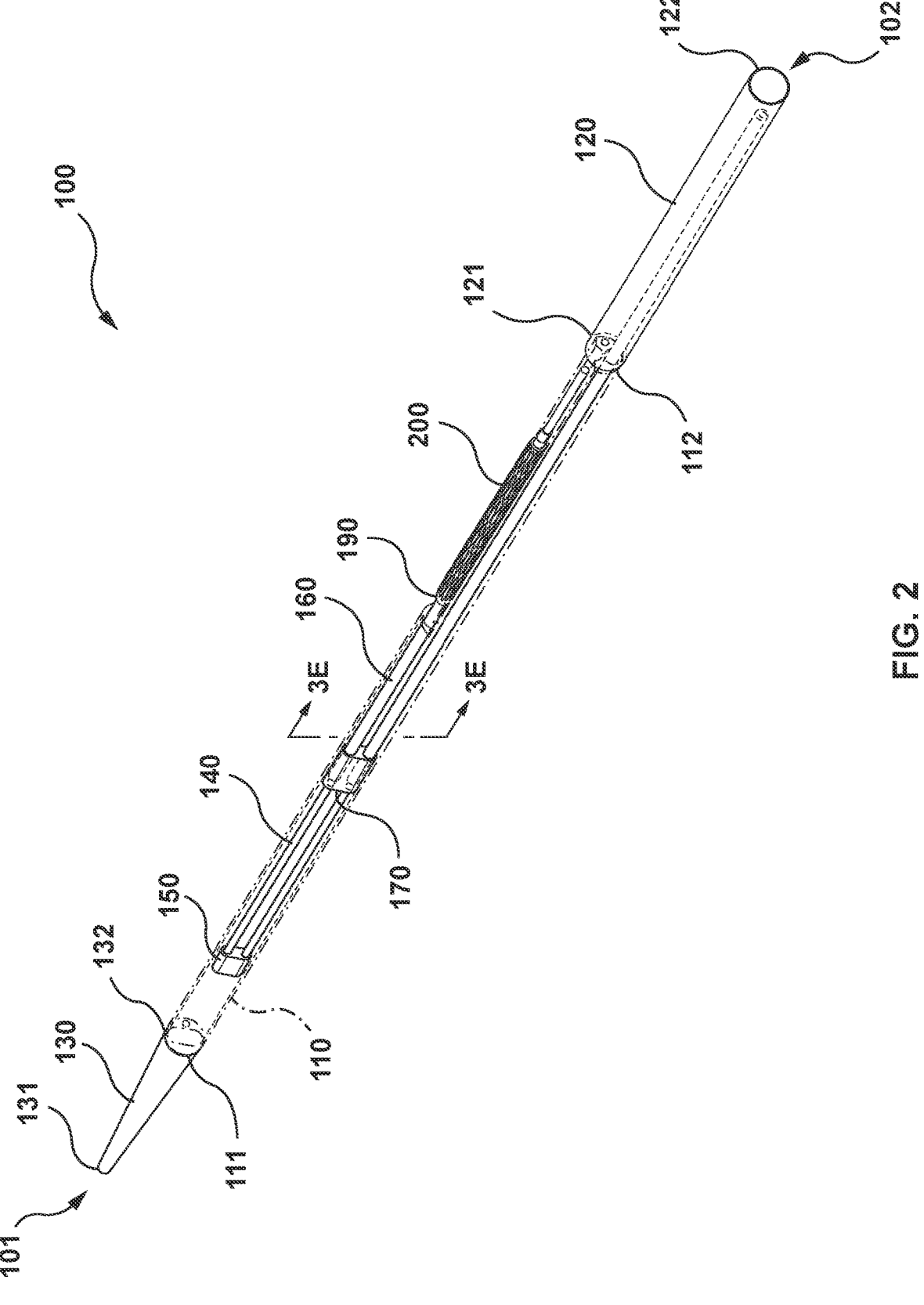
FIG. 2 shows a perspective view of a delivery system according to embodiments hereof.

FIG. 2 shows an exemplary embodiment of a delivery system 100 that may deliver and deploy an internal iliac stent 200 within an internal iliac artery 540 after an iliac branch device 300 is deployed within the corresponding common iliac artery 520 of the vasculature 500 of the patient, which will be described in further detail below. The delivery system 100 includes, inter alia, a shaft 110, a cover 120 and a tip 130.

Figure 3A:
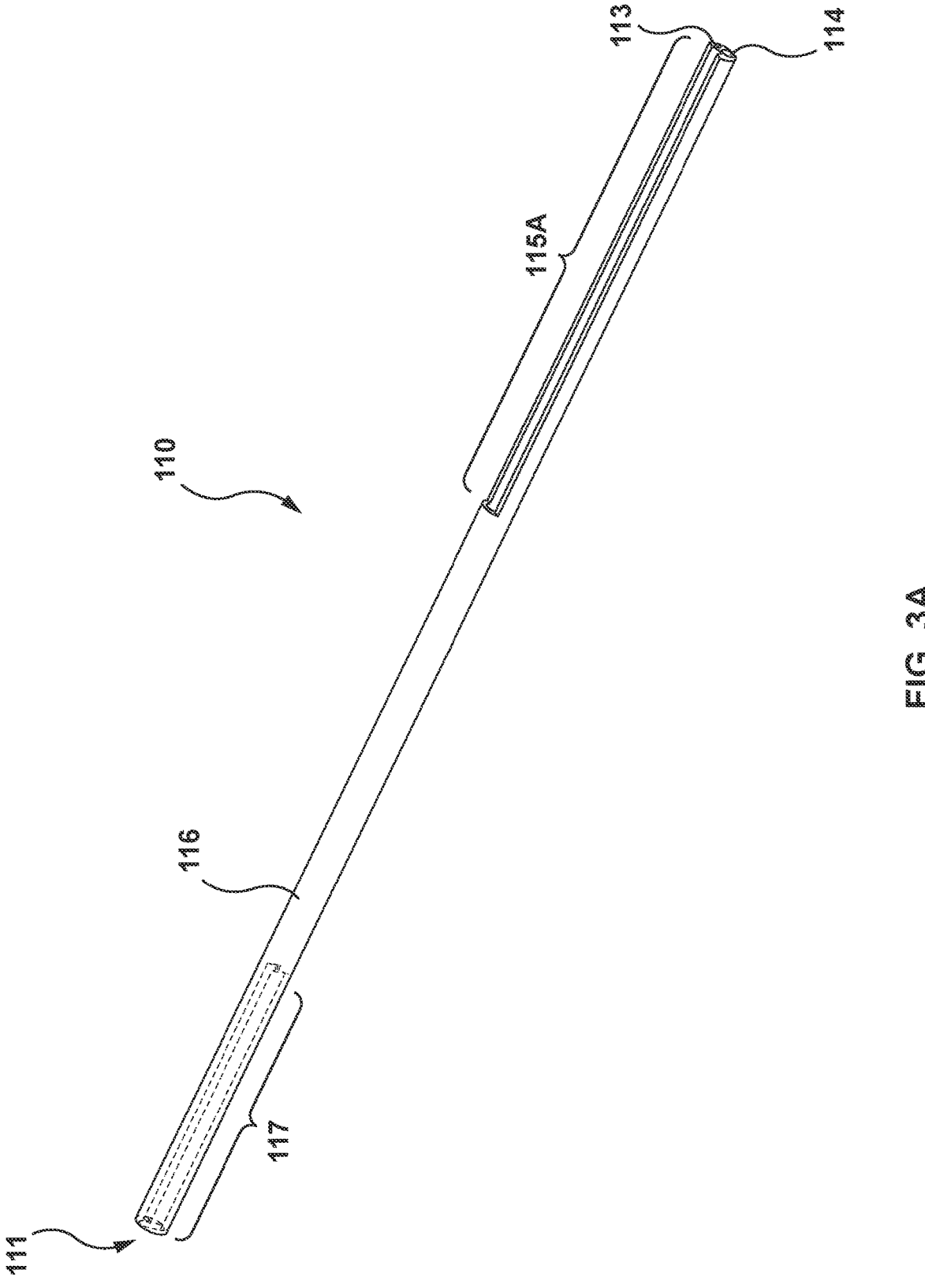
FIG. 3A shows a perspective view of a shaft of the delivery system of FIG. 2 according to embodiments hereof.
Figure 3B:
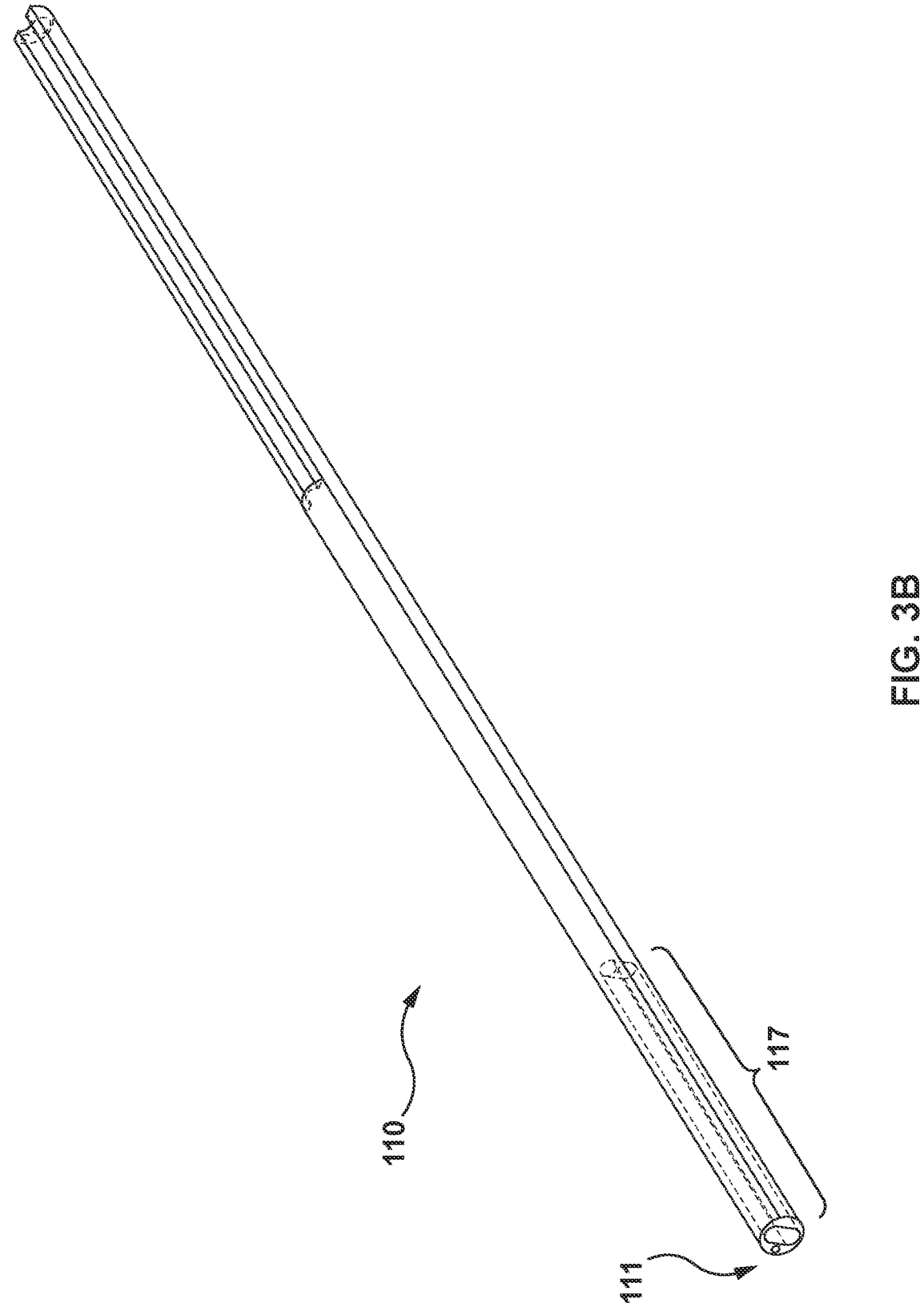
FIG. 3B shows a side view of the shaft of FIG. 3A according to embodiments hereof.
Figure 3C:
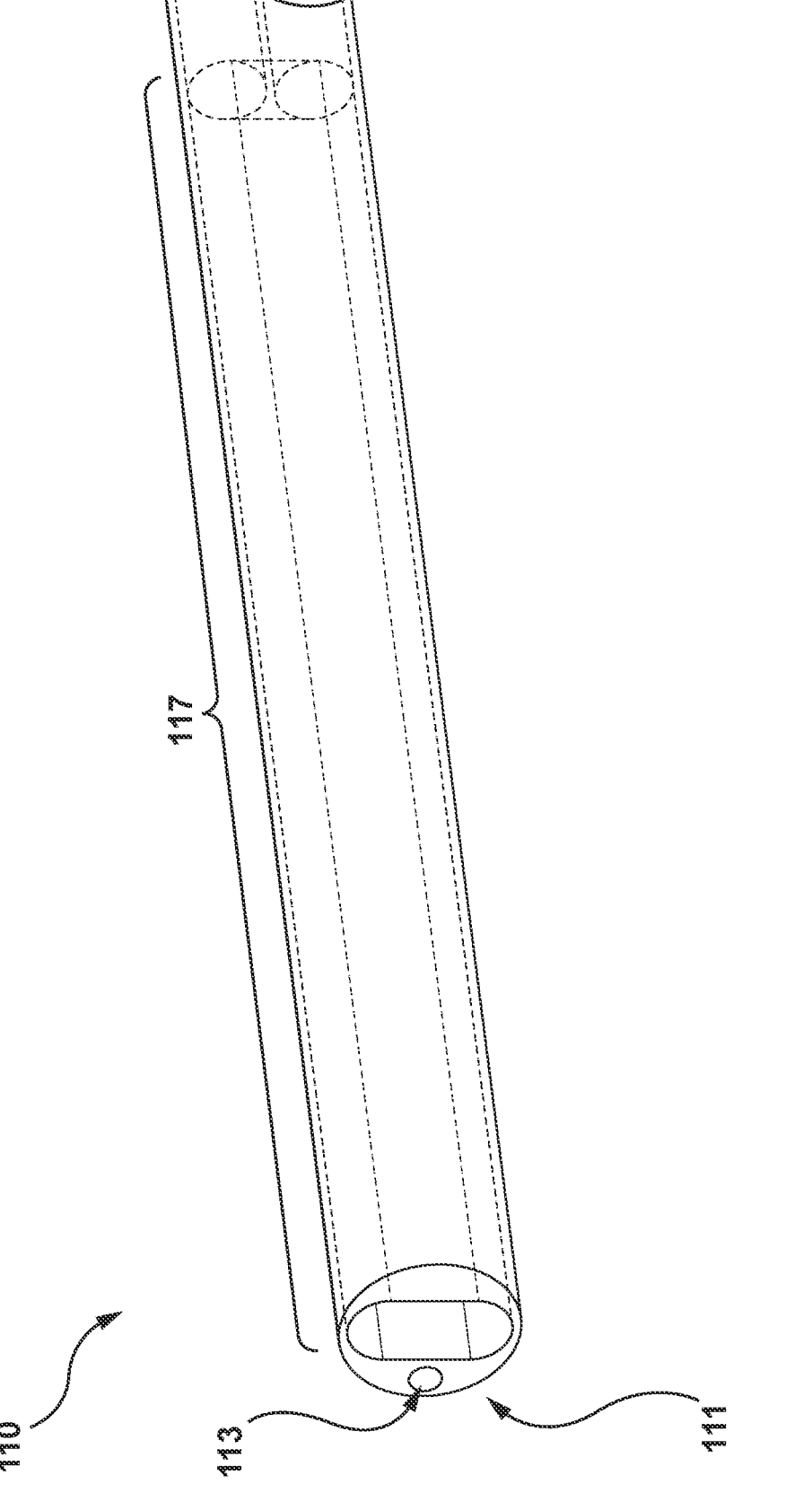
FIG. 3C shows a perspective view of a distal end of the shaft of FIG. 3A according to embodiments hereof.
Figure 3D:
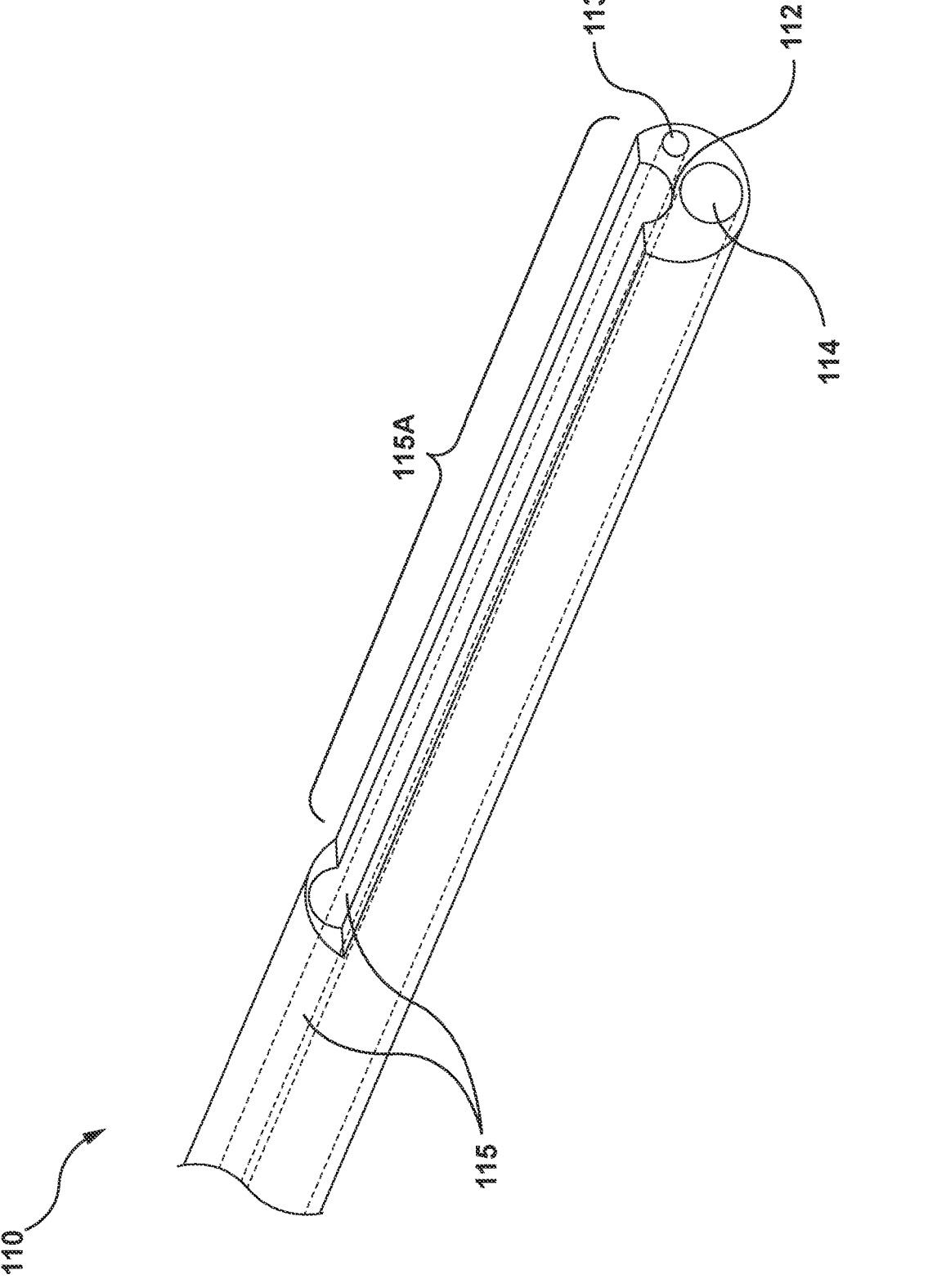
FIG. 3D shows a perspective view of a proximal end of the shaft of FIG. 3A according to embodiments hereof.
Figure 3E:
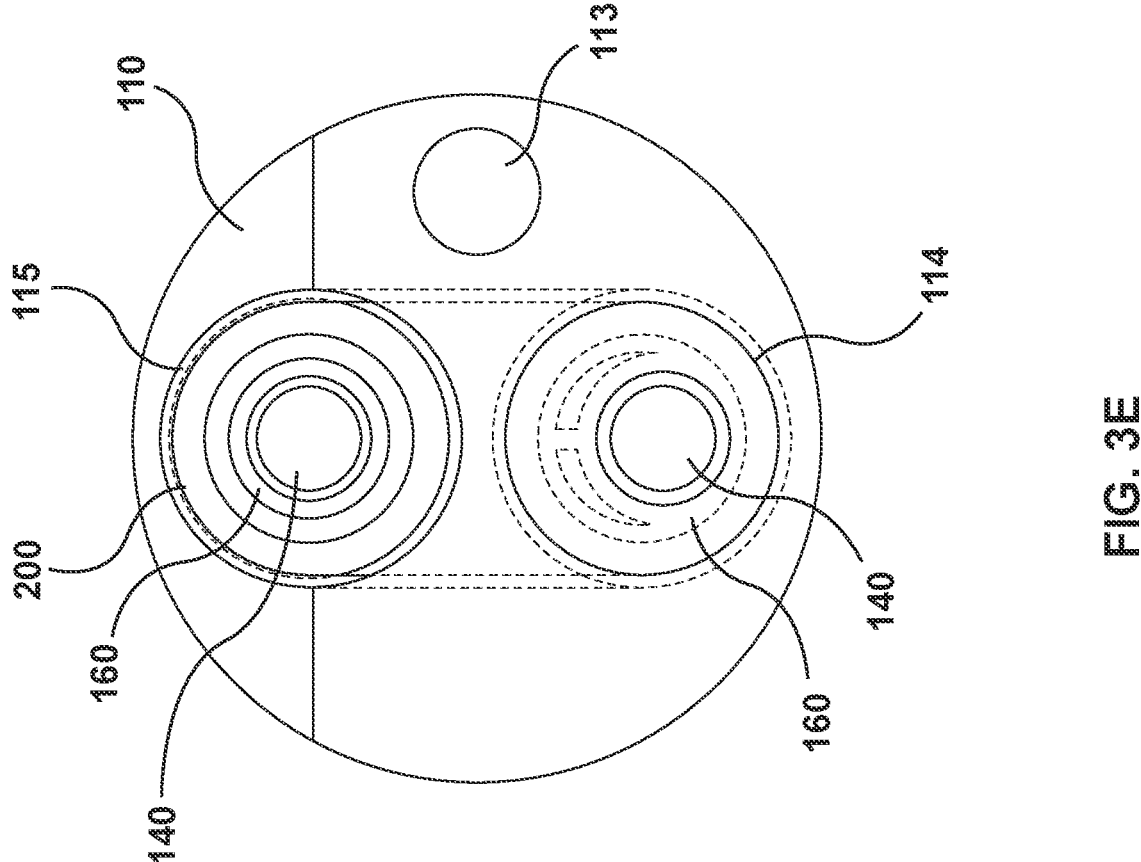
FIG. 3E shows a cross section taken along the line 3E-3E of FIG. 2 according to embodiments hereof.

The shaft 110 of the delivery system 100, as shown in FIG. 2 and FIGS. 3A-3E, is a tubular structure that includes a distal end 111, a proximal end (not shown), an outer surface 116, a guidewire lumen 113, a first main lumen 114, a second main lumen 115, and a skived portion 115A, as will be described in more detail below. The shaft 110 of the delivery system 100 has a cross-section that may be sub-stantially circular, as shown in FIG. 3C. The distal end 111 of the shaft 110 is coupled to the tip 130 of the delivery system 100, described in further detail below, and the proximal end (not shown) of the shaft 110 is coupled to a handle (not shown) of the delivery system 100. The guidewire lumen 113, the first main lumen 114, and the second main lumen 115 are disposed within the outer surface 116 of the shaft 110, as best shown in FIGS. 3D-3E. In the embodiment shown, the guidewire lumen 113 extends an entire longitudinal length of the shaft 110, extending from the distal end 111 to the proximal end (not shown) of the shaft 110. However, in other embodiments, the guidewire lumen 113 need not extend proximally to the handle, such as in a rapid exchange configuration. The guidewire lumen 113 has a diameter that can range from about 0.010 inch to 0.050 inch. The longitudinal length of the shaft 110 can range from about 20 cm to 100 cm. An outer diameter of the shaft 110, defined by the outer surface 116 of the shaft 110, can range from about 12-35 French. The shaft 110 can comprise extruded plastic, molded plastic, polyether block amide (Pebax), polyether ether ketone (PEEK), and/or any other materials known to those skilled in the art.

The first main lumen 114 and the second main lumen 115 extend along at least a portion of the shaft 110. As best shown in FIGS. 3D-3E, the first main lumen 114 and the second main lumen 115 are disposed one-above-the other. However, those skilled in the art would understand that such a description is based on the orientation of the shaft 110, and other orientations, the first and second main lumens 114, 115 may be described as side-by-side. The first and second main lumens 114, 115 are spaced or offset from each other such that they are on different longitudinal axes. For a portion of the shaft 110, the first main lumen 114 and the second main lumen 115 are separated by an internal wall 112. The first main lumen 114 is configured to house a first member 163 of a delivery device 160 and the second main lumen 115 is configured to house a second member 166 of the delivery device 160, as explained in more detail below. The first main lumen 114 may extend proximally to a proximal end of the delivery system 100. The second main lumen 115 need not extend proximally the proximal end of the delivery system 100, and preferably only extends proximally to a proximal end of a skived portion 115A of the second main lumen 115, described in more detail below. At the distal end 111 of the shaft 110, the first main lumen 114 and the second main lumen 115 connect, or combine, at a U-turn lumen 117 of the shaft 110. In other words, at the U-turn lumen 117 of the shaft 110, the internal wall 112 is eliminated such that the first and second main lumens 114, 115 form a single, enlarged lumen that is oval-shaped in the embodiment shown, as best shown in FIG. 3C. The first main lumen 114, the second main lumen 115 and the U-turn lumen 117 within the shaft 110 create a U-shaped lumen within the shaft 110, with the U-turn lumen 117 disposed at the distal end 111 of the shaft 110. Thus, the shaft 110, along a proximal portion thereof may include the guidewire lumen 113 and the first main lumen 114. At a distal portion of the shaft 110, the shaft

110 includes the guidewire lumen, the first main lumen 114, and the second main lumen 115. At a distal end 111 of the shaft 110, the shaft 110 includes the guidewire lumen 113 and the U-turn lumen 117. The U-turn lumen 117 is of sufficient length to enable a manifold 170 (described below) connecting the first and second members 163, 166 of the delivery device 160 and a stylet connector 150 (described below) to slide sufficiently to move the second portion 160B of the delivery device 160 a desired length to extend into a branch vessel, as described in more detail below. In an example, the U-turn lumen 117 may be a length of 2 to 20 cm.

As briefly noted above, the shaft 110 further includes the skived portion 115A, as best shown in FIG. 3D. At the skived portion 115A a portion of the outer wall of the shaft 110 is removed so as to expose the second lumen main lumen 115. As described in more detail below, the skived portion 115A enables the second portion 160B of the delivery device 160 to angle outward relative to the central longitudinal axis of the shaft 110 to enter a branch vessel. The portion of the outer wall of the shaft 110 that is removed to create the skived portion 115A is on the opposite side of the second main lumen 115 as the first main lumen 114. For example, if the shaft 110 is oriented with the second main lumen 115 above the first main lumen 114, the portion of the outer wall of the shaft 110 that is removed is above the second main lumen 114, or a top portion of the shaft 110. The portion of the outer wall that is removed to create the skived portion 115A of the second main lumen 115 does not overlap with the guidewire lumen 113 or the first main lumen 114 of the shaft 110. In other words, the skived portion 115A of the second main lumen 115 does not expose the guidewire lumen 113 or the first main lumen 114. The circumferential portion of the outer wall that is removed to create the skived portion 115A of the second main lumen 115 is sufficient to enable the second portion 160B of the delivery device 160 to exit the second main lumen 115. In an embodiment, about half of the circumference of the second main lumen 115 is exposed. The longitudinal length of the skived portion 115A of the shaft 110 can range from about 2 cm to the longitudinal length of second main lumen 115 of the shaft 110.

Figure 4A:
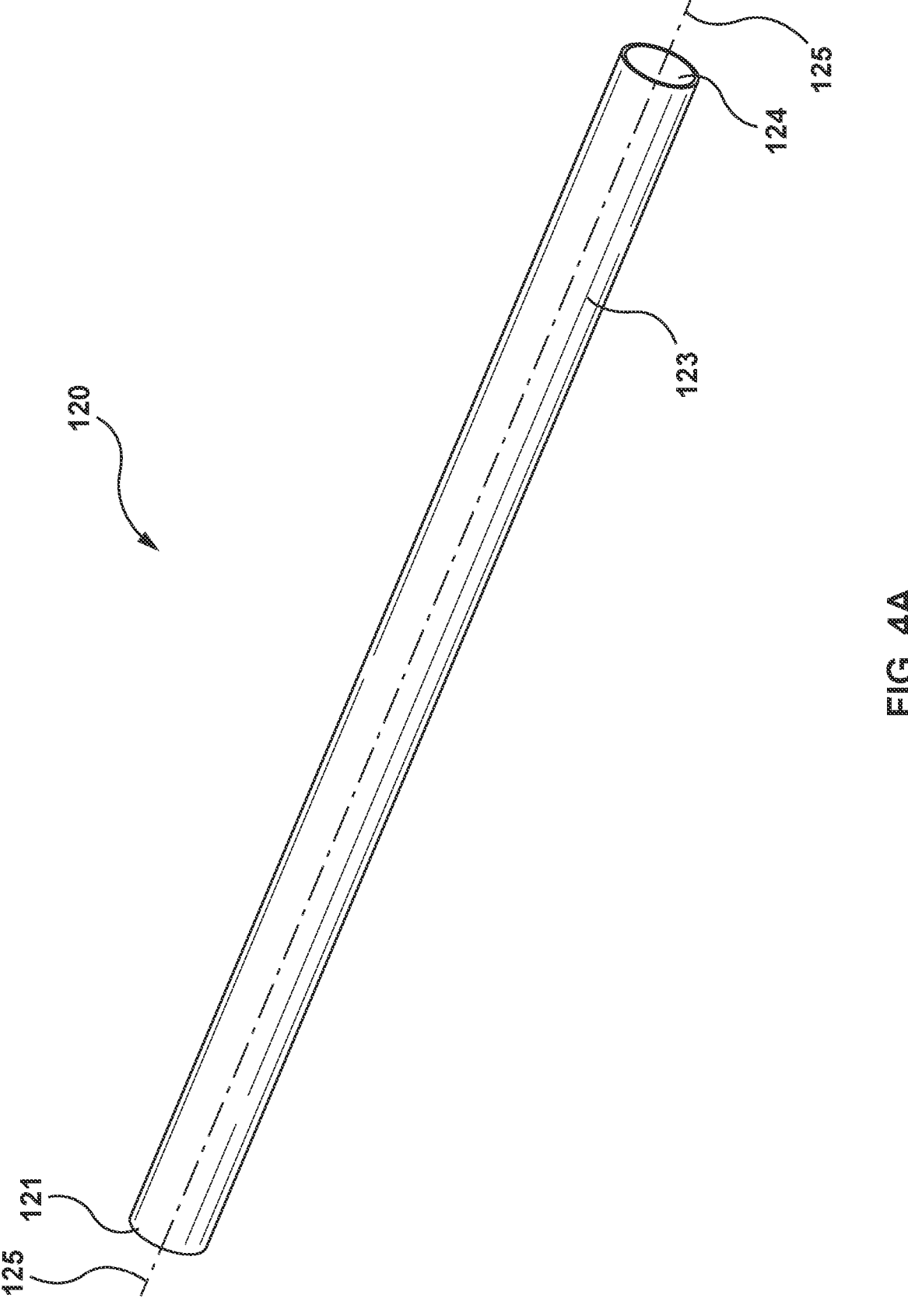
FIG. 4A shows a perspective view of a cover of the delivery system of FIG. 2 according to embodiments hereof.
Figure 4B:
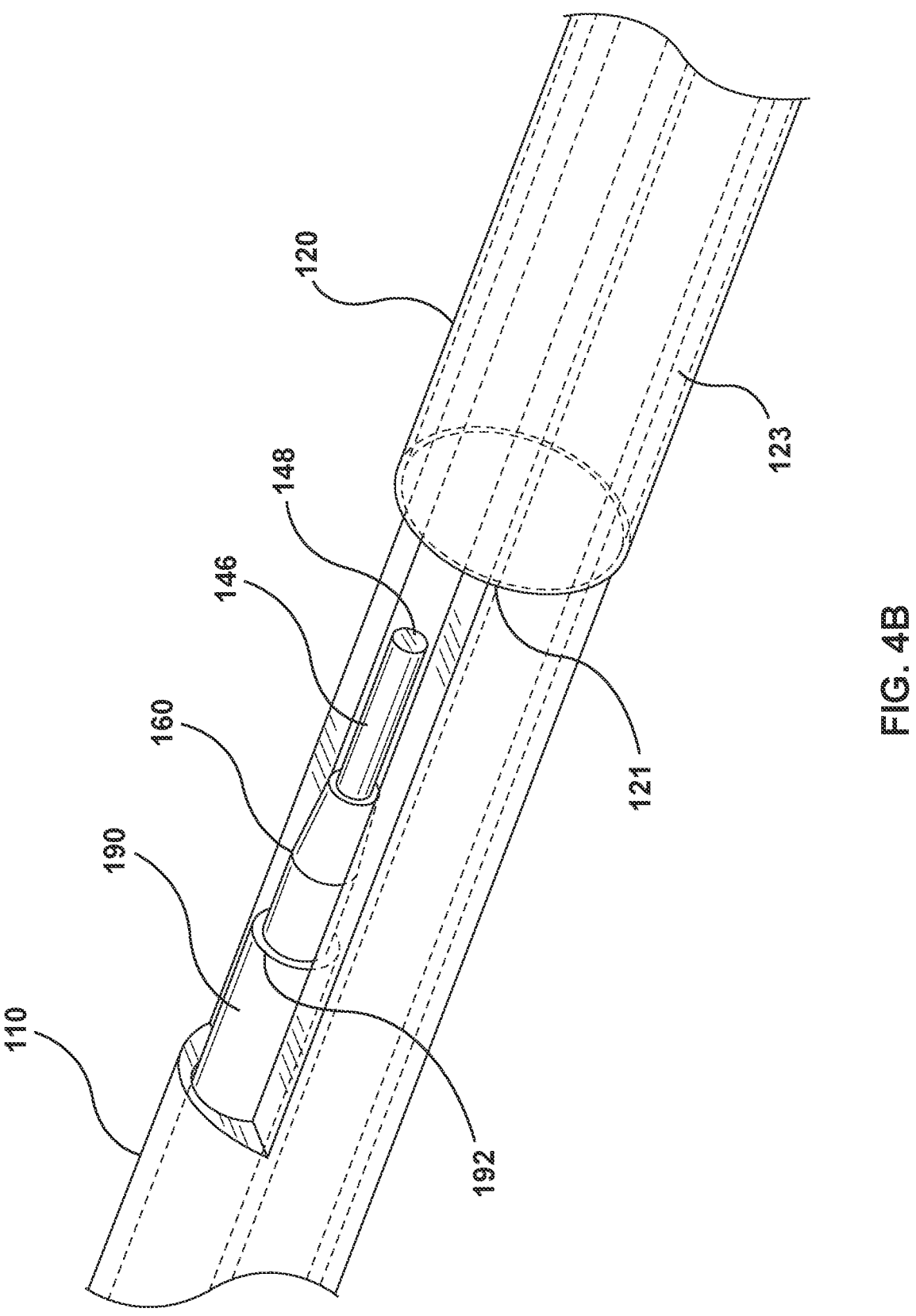
FIG. 4B shows the skived portion of FIG. 3D and the cover of FIG. 4A according to embodiments hereof.

The cover 120 of the delivery system 100, as shown in FIG. 2 and FIGS. 4A-4B, is a tubular piece or structure that includes a distal end 121, a proximal end (not shown), an outer surface 123, and an inner surface 124 that defines a central lumen 125 therethrough. The proximal end (not shown) of the cover 120 is coupled to the handle (not shown) of the delivery system 100, such as to an actuator (not shown) to enable proximal and distal movement of the cover 120 relative to the shaft 110. The central lumen 125 of the cover 120 may extend an entire longitudinal length of the cover 120. The central lumen 125 of the cover 120 may have a substantially circular cross-section. The central lumen 125 is sized and shaped to slidably fit the shaft 110 therethrough, as shown in FIG. 4B. The cover 120 is configured to slide over the shaft 110 to cover or enclose and uncover the skived portion 115A of the shaft 110, as described in more detail below. The cover 120 has an inner diameter, defined by the inner surface 124 of the cover 120, that can range from about 12-35 French. The cover 120 has an outer diameter, defined by the outer surface 123 of the cover 120, that can range from about 12-35 French. The cover 120 has a longitudinal length that can range from about 20-100 cm. The cover 120 can comprise extruded plastic, molded plastic, polyether block amide (Pebax), polyether ether ketone (PEEK), and/or any other materials known to those skilled in the art.

Figure 5A:
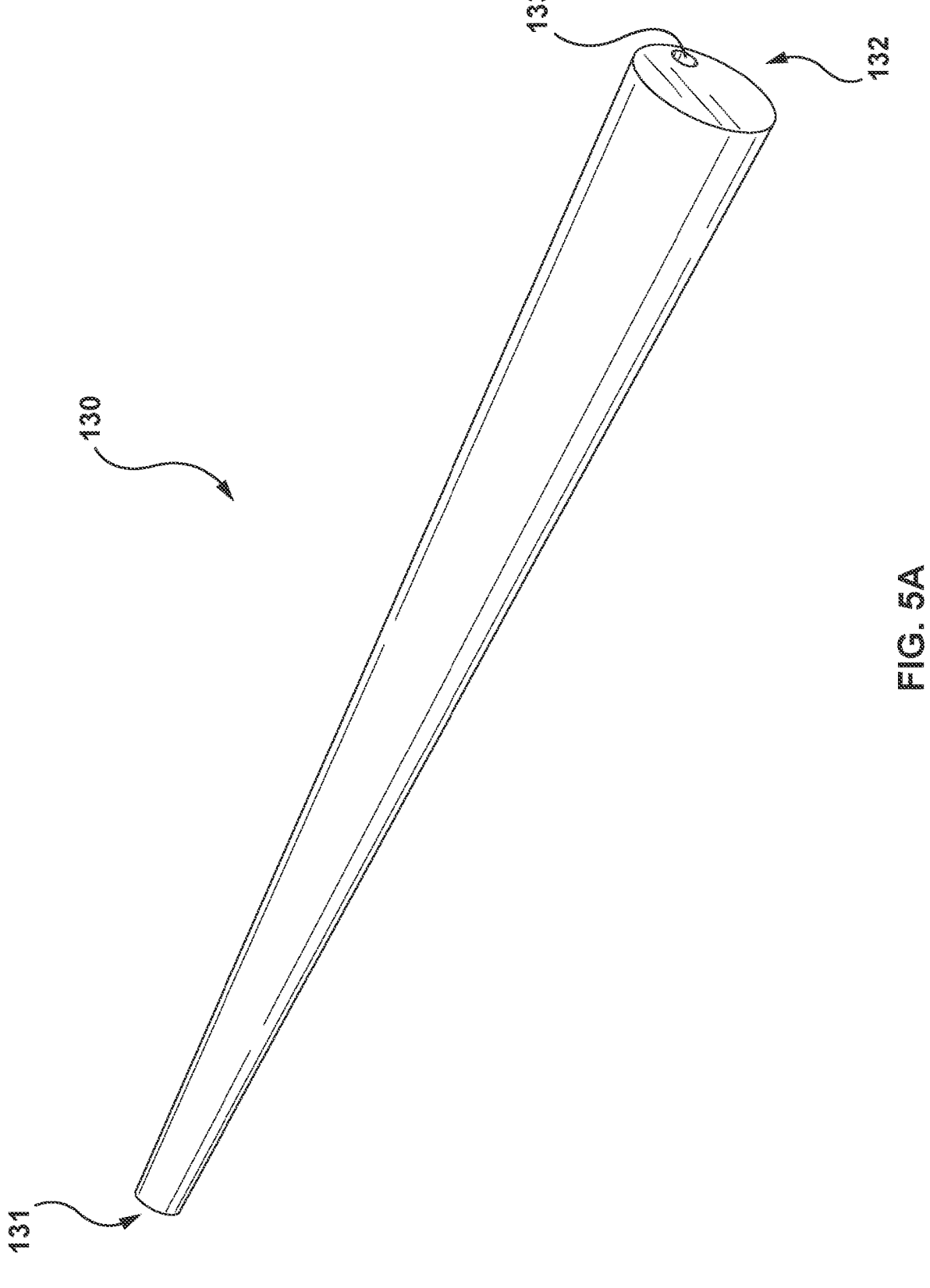
FIG. 5A shows a perspective view of a tip of the delivery system of FIG. 2 according to an embodiment hereof
Figure 5C:
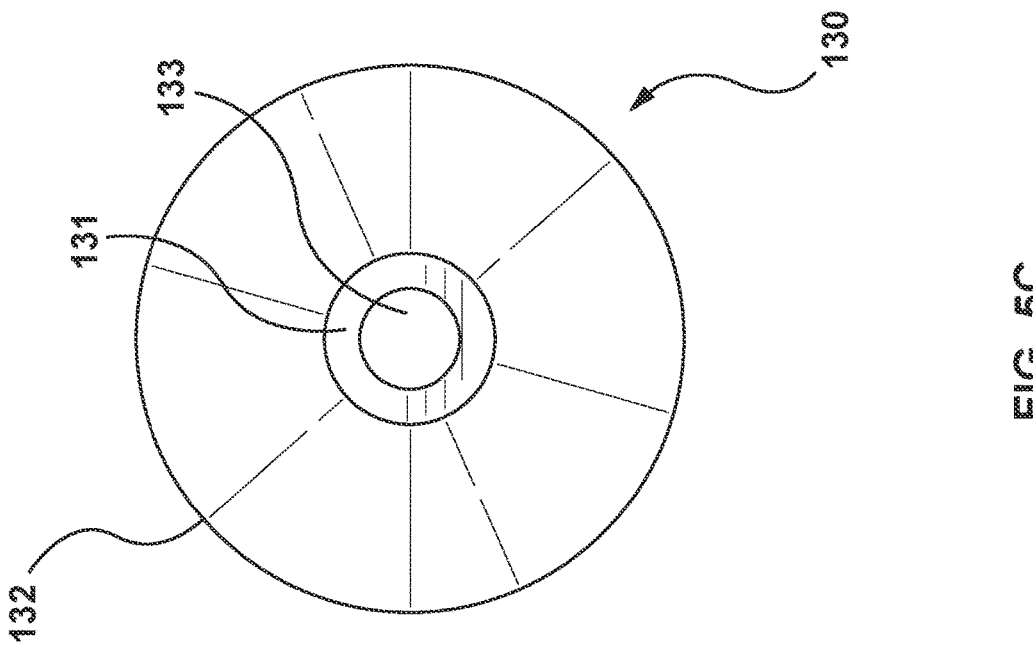
FIG. 5C shows a distal end of the tip of FIG. 5A according to embodiments hereof.
Figure 5B:
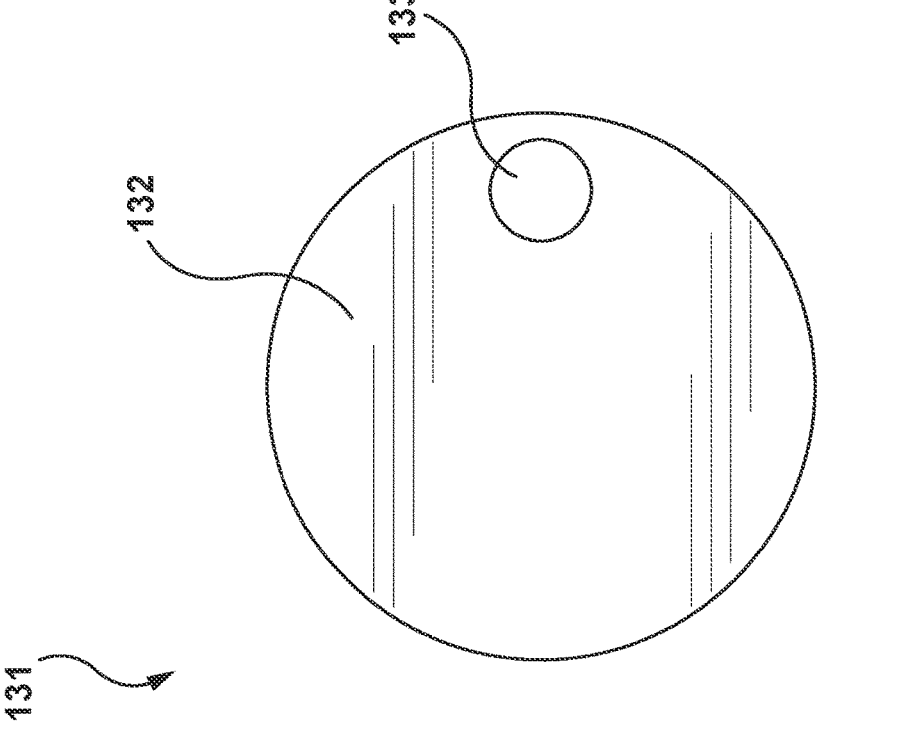
FIG. 5B shows a proximal end of the tip of FIG. 5A according to embodiments hereof.

The tip 130 of the delivery system 100, as shown in FIG. 2 and FIGS. 5A-5C, is a tapered structure that includes a distal end 131, a proximal end 132, and a guidewire lumen 133 extending from the proximal end 132 to the distal end 131. The proximal end 132 of the tip 130 is coupled to the distal end 111 of the shaft 110 such that the guidewire lumen 113 of the shaft 110 is in communication with the guidewire lumen 133 of the tip 130. The distal end 131 and the proximal end 132 of the tip 130 may have substantially circular cross-sections, as shown in FIGS. 5B-5C. The tip 130 tapers in a distal direction such that a diameter of the distal end 131 of the tip 130 is smaller than a diameter of the proximal end 132 of the tip 130, as best seen in FIG. 5A. The diameter of the distal end 131 of the tip 130, as shown in FIG. 5C, can range from about 0.01 inch to 0.10 inch while the diameter of the proximal end 132 of the tip 130, as shown in FIG. 5B, can range from about 12-35 French. In the embodiment shown, the guidewire lumen 133 at the proximal end of the tip 130 is offset from the central longitudinal axis of the tip 130 to align with the guidewire lumen 113 of the shaft 110, as shown in FIG. 5B. At the distal end 131 of the tip 130, the guidewire lumen 133 is aligned with the central longitudinal axis of the tip 130. The longitudinal length of the tip 130 can range from about 1 to 10 cm. The tip 130 can comprise molded plastic, overmolded plastic, polyether block amide (Pebax), and/or any other materials known to those skilled in the art.

Figure 6:
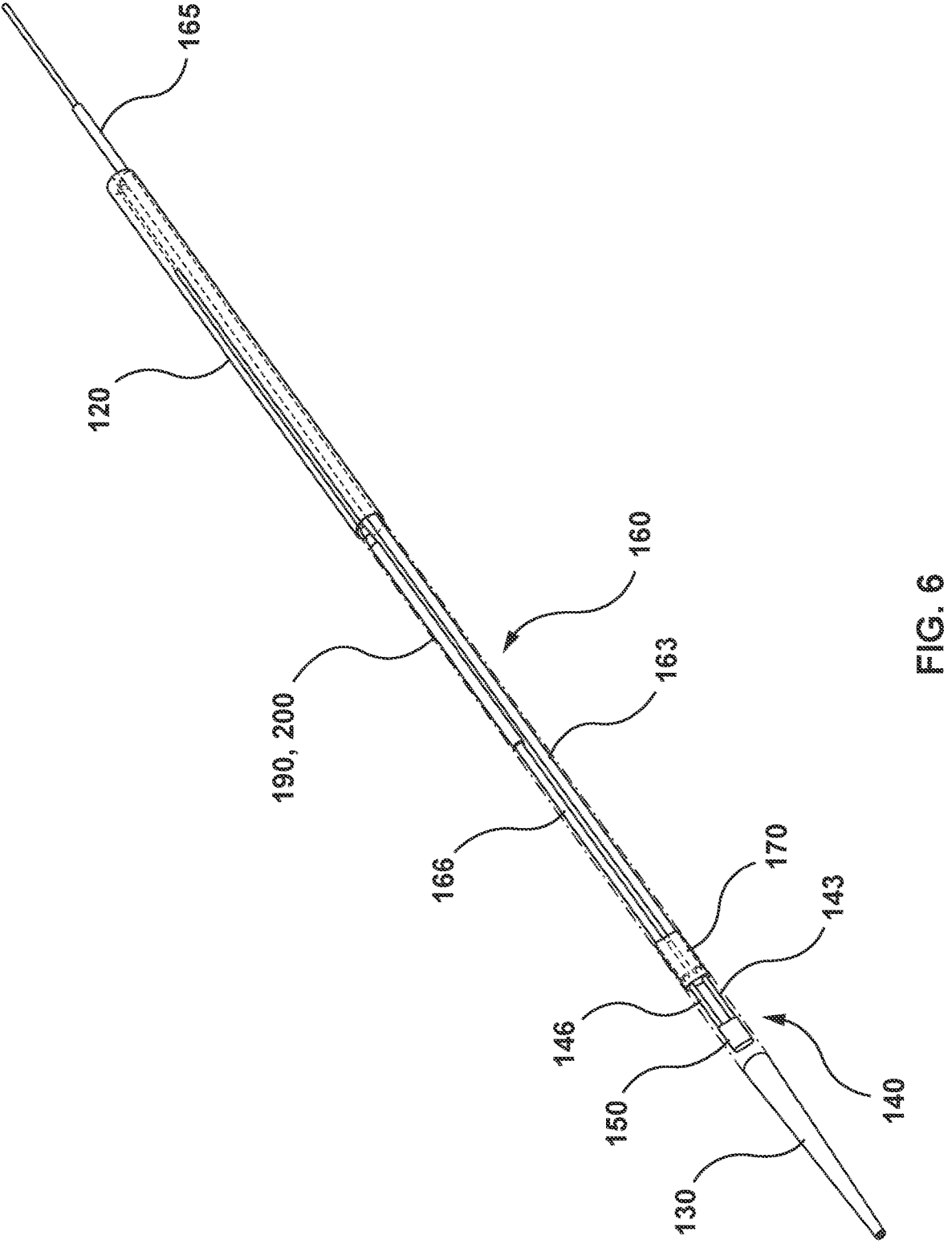
FIG. 6 shows a perspective view of the delivery system according to embodiments hereof.

As noted above, the delivery system 100 also includes a delivery device 160. FIG. 6 shows the delivery device 160 with its constituent parts within the shaft 110 of the delivery system 100 according to embodiments herein. Also associated with the delivery device 160 is a stylet 140 and an internal iliac stent graft 200, as will be described in more detail below. The delivery device 160, as shown in FIG. 6 and FIGS. 8A-8K, includes the first member 163, the second member 166, and a U-turn manifold 170, as briefly mentioned above and described in more detail below.

Figure 8A:
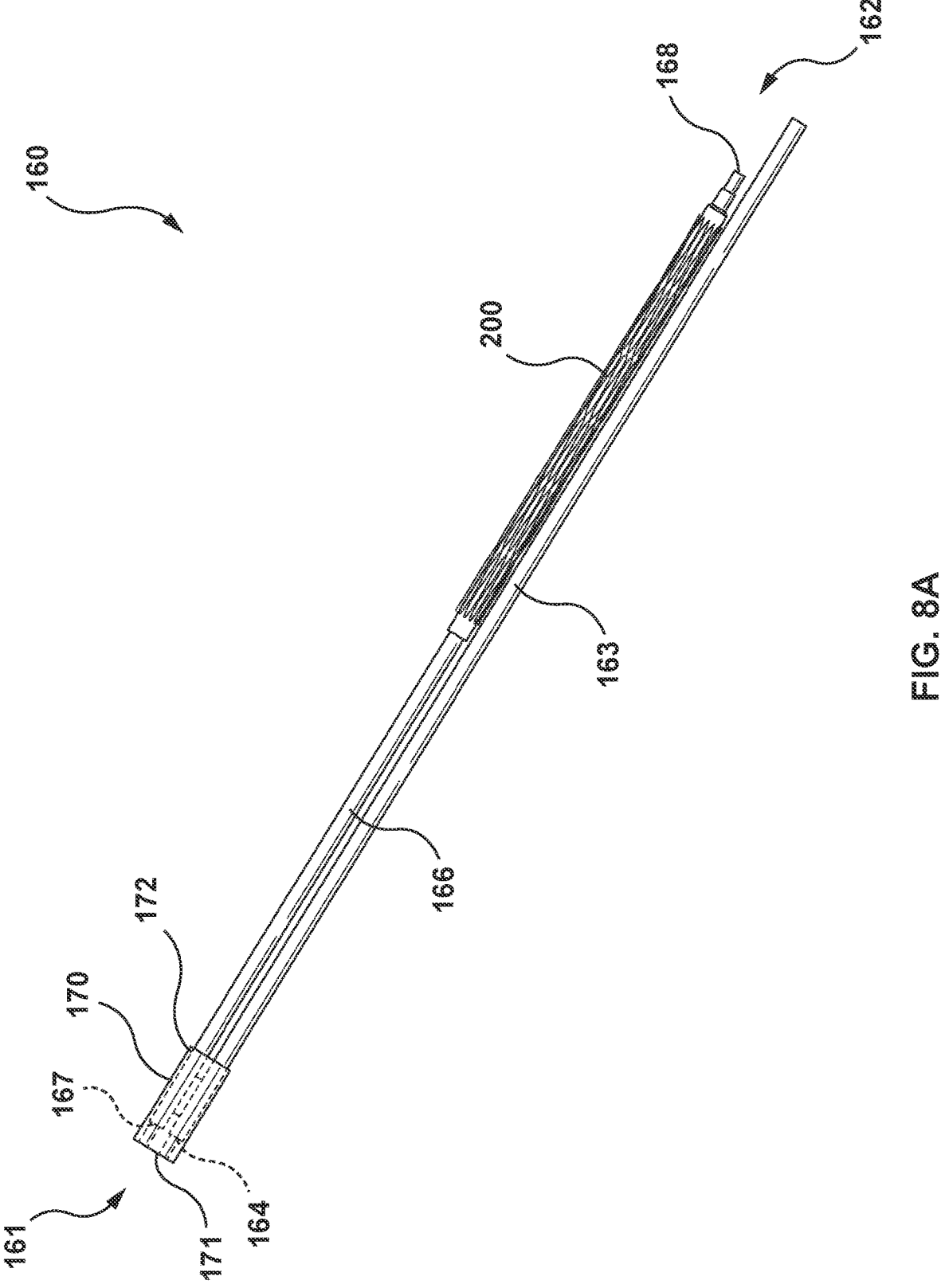
FIG. 8A shows a perspective view of a delivery device of the delivery system of FIG. 6 according to embodiments hereof.

FIG. 8A shows the delivery device 160 separated from the delivery system 100. The delivery device 160 generally described includes the first member 163 extending from a proximal end (not shown) distally to a distal end 164 coupled the manifold 170 and the second member 166 extending from a distal end 167 coupled to the manifold and extending proximally back to a proximal end 168 of the second member 166. The first member 163 and the second member 166 are spaced or offset from each other such that the first member 163 and the second member 166 extend along different longitudinal axes.

Figure 8B:
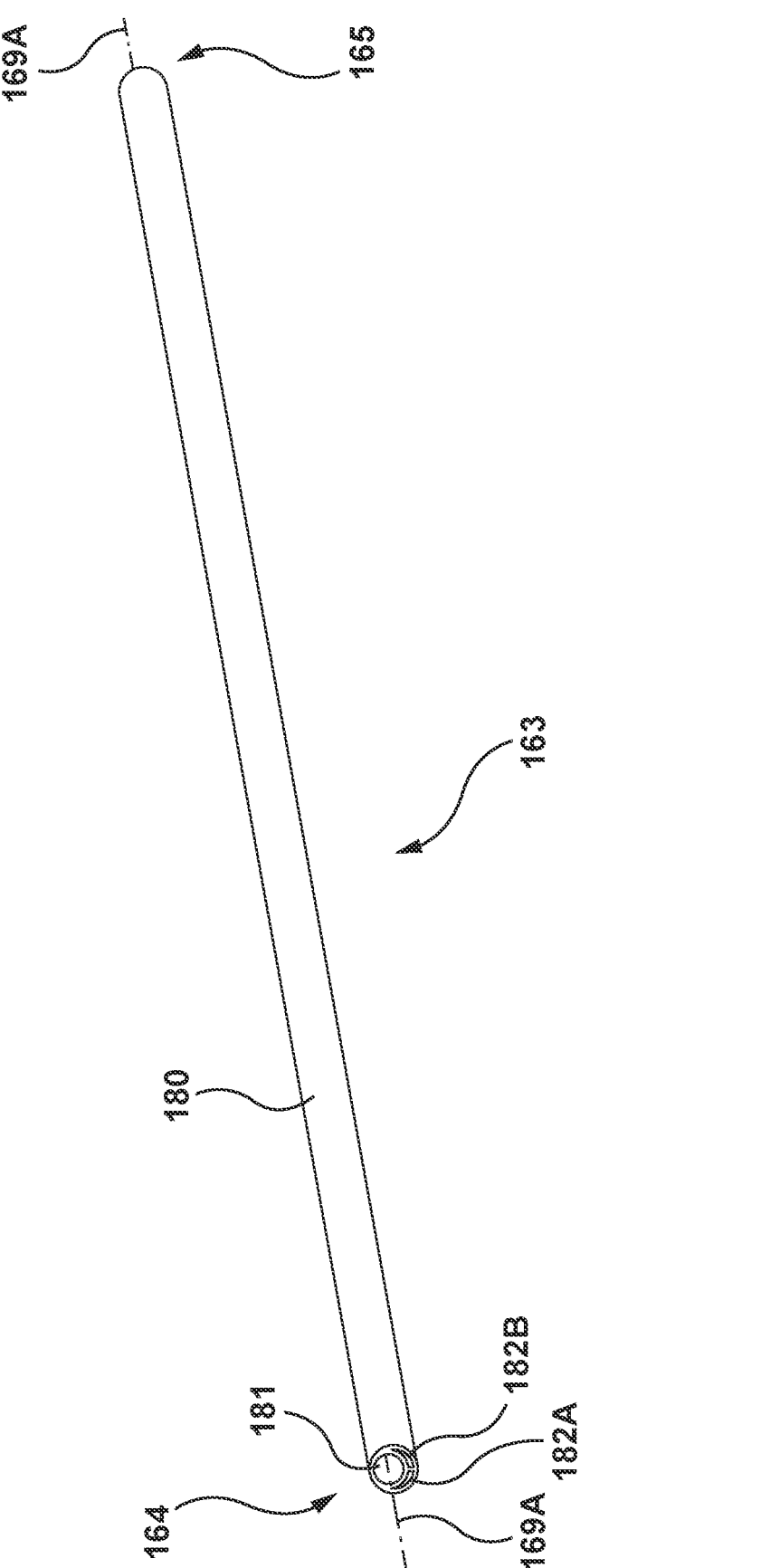
FIG. 8B shows a perspective view of a first member of the delivery device of FIG. 8A according to embodiments hereof.
Figure 8C:
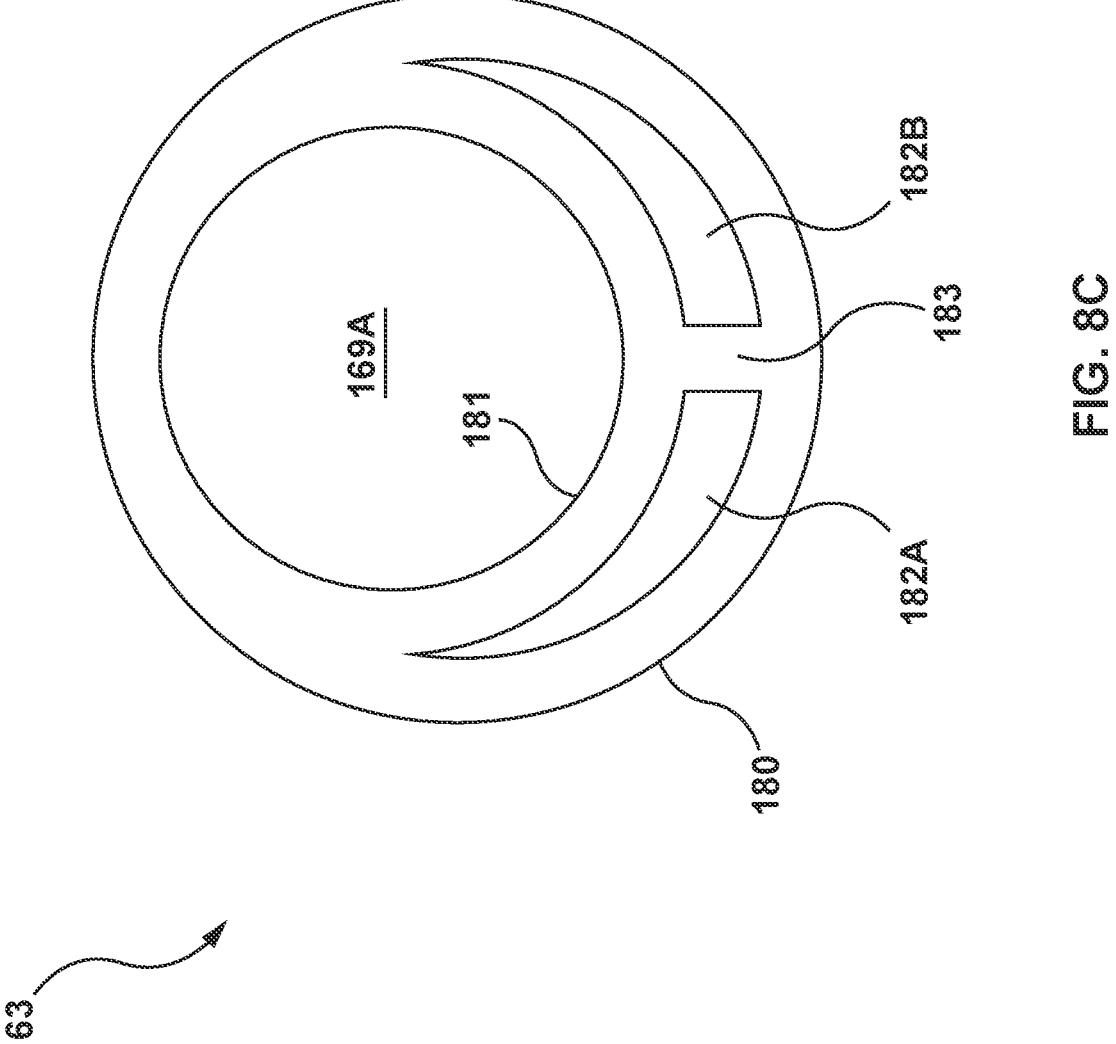
FIG. 8C shows a cross-section of the first member of FIG. 8B according to embodiments hereof.

An embodiment of the first member 163 of the delivery device 160 is shown in FIGS. 8B-8C. In the embodiment shown, the first member 163 including a first central lumen 169A and an outer lumen 182. The first member 163 may have a substantially circular cross-section defined by an outer surface 180. An inner surface 181 of the first member 163 defines the first central lumen 169A. The first central lumen 169A may have a substantially circular cross-section and extends an entire longitudinal length of the first member 163, as shown in FIG. 8B. The first central lumen 169A is sized and shaped to slidably receive a first wire member 143 of the stylet 140 therewithin, as described in further detail below. A diameter of the first central lumen 169A of the first member 163 may range from about 0.05 inch to 0.20 inch. A longitudinal length of the first member 163 of the stent delivery device 160 may range from about 20 to 100 cm.

FIG. 8C shows a cross-section an embodiment of the first member 163 of the stent delivery device 160. In the embodiment shown, the first central lumen 169A is offset from a central longitudinal axis of the first member 163 and the outer lumen 182 is disposed radially outside of the first central lumen 169A to one side (under in FIG. 8C) of the first central lumen 169A. Further, in the embodiment shown, the outer lumen 182 extends partially around the circumference of the first central lumen 169A and is separated into a first outer lumen portion 182A and a second outer lumen portion 182B by a radially extending wall 183. The outer lumen 182 may also be referred to as an inflation lumen, as it is configured to deliver inflation fluid to a balloon of the delivery device 160, as described in more detail below. The embodiment described with respect to the first central lumen 169A and the outer lumen 182 is not meant to be limiting, and other configurations of a balloon catheter may be utilized. For example, and not by way of limitation, the outer lumen 182 may extend around the entire circumference of the first central lumen 169A in an annular inflation lumen configuration.

Figure 8D:
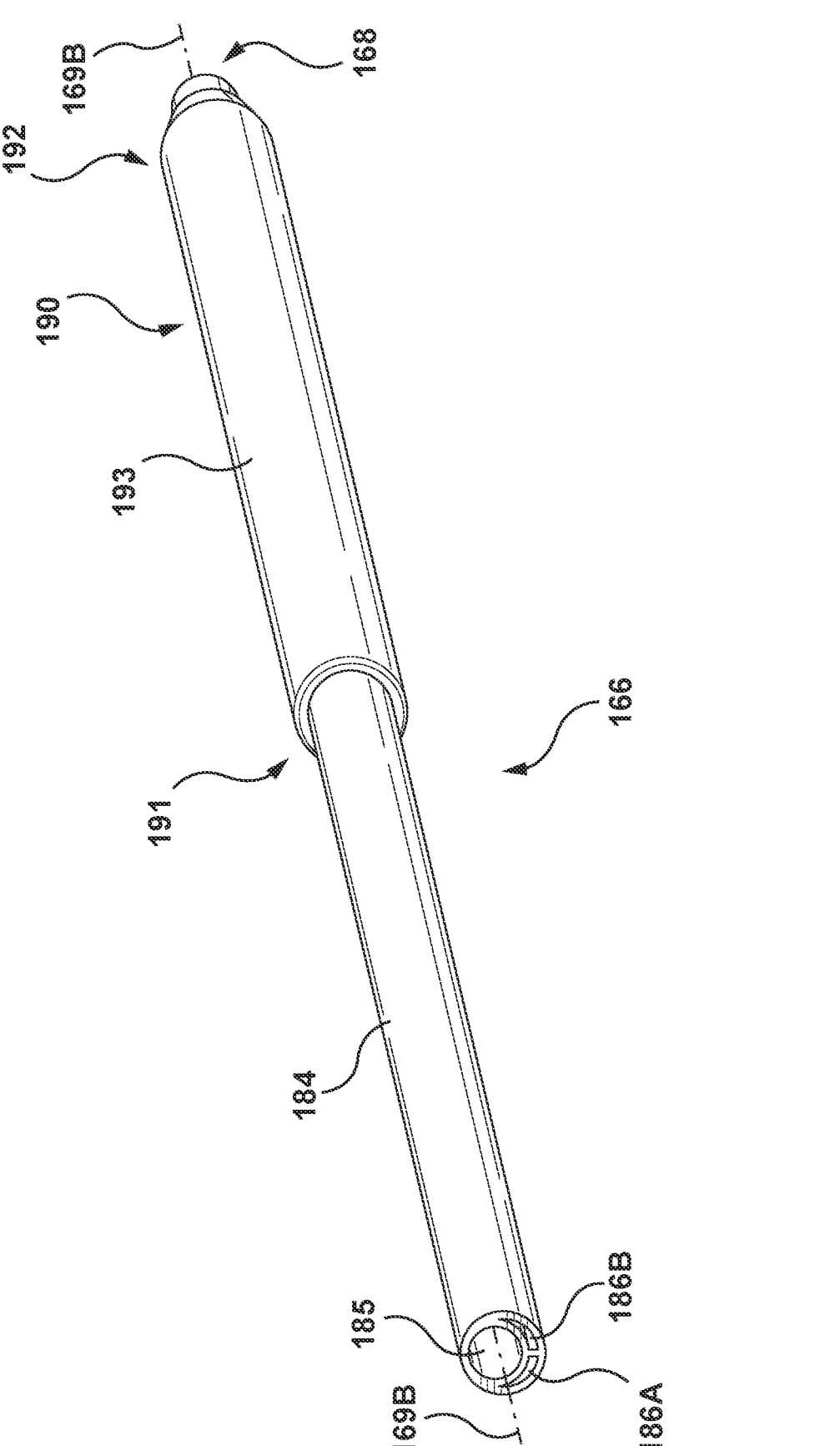
FIG. 8D shows a perspective view of a second member of the delivery device of FIG. 8A and a stent according to embodiments hereof.
Figure 8E:
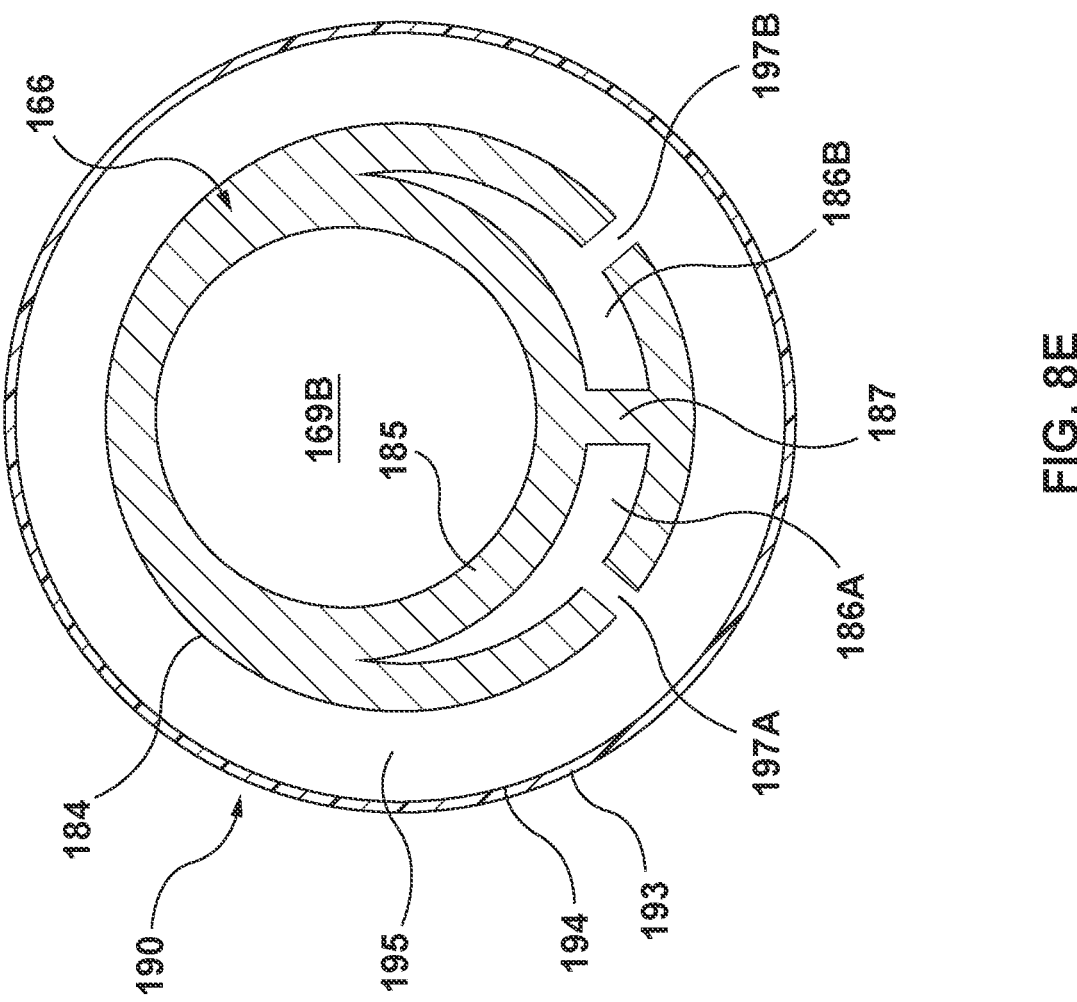
FIG. 8E shows a cross section of a proximal end of the second member of FIG. 8D according to embodiments hereof.
Figure 8F:
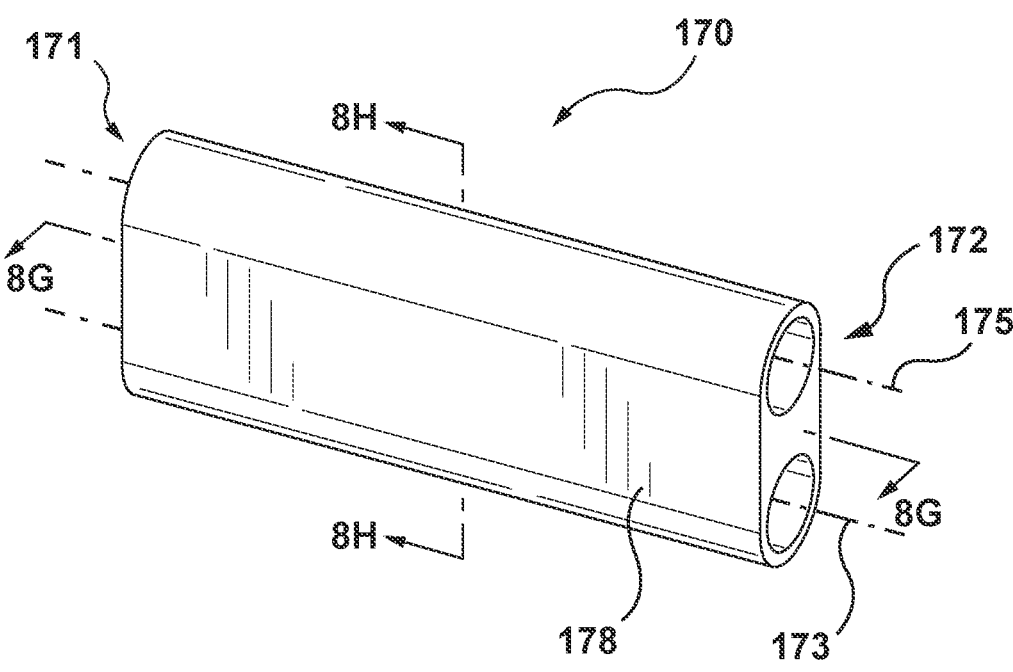
FIG. 8F shows a perspective view of a U-turn manifold of the delivery device of FIG. 8A according to embodiments hereof.

An embodiment of the second member 166 of the stent delivery device 160 is shown in FIGS. 8D-8E. The second member 166 may be a tubular structure that may be substantially similar to the first member 163 described above. As noted above, the second member 166 includes the distal end 167 coupled to the manifold 170 and extends proximally to the proximal end 168. The second member 166, similar to the first member 163, includes a second central lumen 169B and an outer lumen 186. The second member 166 further includes a balloon 190 coupled thereto, as described in more detail below. As with the first member 163, the second member 166 may have substantially circular cross-section defined by an outer surface 184. The second central lumen 169B may have a substantially circular cross-section and extends an entire longitudinal length of the second member 166, from the distal end 167 to the proximal end 168 of the second member 166. The second central lumen 169B is sized and shaped to slidably receive a second wire member 146 of the stylet 140 therewithin, which will be described in further detail below. A diameter of the second central lumen 169B of the second member 166 of the stent delivery device 160 can range from about 0.05 inch to 0.20 inch. The longitudinal length of the first member 163 is longer than a longitudinal length of the second member 166 of the stent delivery device 160, as the first member 163 extends proximally outside of the body and the second member 166 is configured to be disposed into a branch vessel, such as the internal iliac/hypogastric artery, as described in more detail below. The longitudinal length of the second member 166, from the distal end 167 to the proximal end 168, can range from about 10 to 100 cm.

FIG. 8E shows a cross-section of the proximal end 168 of the second member 166 of the stent delivery device 160. In the embodiment shown, the second central lumen 169B is offset from a central longitudinal axis of the second member 166 and the outer lumen 186 is disposed radially outside of the second central lumen 169B to one side (under in FIG. 8E) of the second central lumen 169B. Further, in the embodiment shown, the outer lumen 186 extends partially around the circumference of the second central lumen 169B and is separated into a first outer lumen portion 186A and a second outer lumen portion 162B by a radially extending wall 187. The outer lumen 186 may also be referred to as an inflation lumen, as it is configured to delivery inflation fluid to the balloon 190. In the embodiment shown, the outer lumen 186 (i.e., the first outer lumen portion 186A and the second outer lumen portion 186B) terminate prior to the proximal end 168 of the second member 166 such that inflation fluid in the outer lumen 186 is contained therein except for inflating the balloon, as described below. The embodiment described with respect to the second central lumen 169B and the outer lumen 186 is not meant to be limiting, and other configurations of a balloon catheter may be utilized. For example, and not by way of limitation, the outer lumen 186 may extend around the entire circumference of the second central lumen 169A in an annular inflation lumen configuration.

The balloon 190 of the second member 166 is configured to inflate and expand the stent graft 200 disposed thereon, which will be described in further detail below. The balloon includes a distal end 191, a proximal end 192, an outer surface 193, an inner surface 194, and an interior cavity 195, as best shown in FIG. 8E, which shows the balloon 190 separated from the outer surface 184 of the second member 166 for clarity or is in at least a partially expanded configuration of the balloon 190. With the balloon 190 deflated, the inner surface 194 of the balloon 190 would generally lie against the outer surface 184 of the second member 166. As shown schematically in FIG. 8D, the distal end 191 of the balloon 190 and the proximal end 192 of the balloon 190 are attached to the outer surface 184 of the second member 166, such as by melding. However, this is not meant to be limiting. For example, and not by way of limitation, in an annular inflation lumen arrangement, an outer shaft of the second member may terminate distally of an inner shaft of the second member (normally proximally but the second member is arranged opposite in the delivery device 160) such that the distal end 191 of the balloon 190 would be attached to such an outer shaft and the proximal end 192 of the balloon 190 would be attached to such an inner shaft, with the annular inflation lumen being open to the interior cavity 195 of the balloon 190 at an open terminal end of the inflation lumen. The balloon 190 may be any material used for balloons of balloon catheters, such as, but not limited to, nylon and/or polyester.

Within the longitudinal length of the balloon 190, inflation fluid from the first outer lumen portion 186A and the second outer lumen portion 186B needs to exit the respective lumen and enter into the interior cavity 195 of the balloon 190. Therefore, longitudinally between the where the distal end 191 and the proximal end 192 of the balloon 190 attach to the outer surface 184 of the second member 166, radial channels or openings 197A, 197B extend from the interior of the respective first and second outer lumen portions 186A, 186B through the outer surface 184 of the second member 166, such that inflation fluid may exit each of the first and second outer lumen portions 186A, 186B into the interior cavity 195 of the balloon 190. The cross-section of FIG. 8E is taken at a longitudinal location between the proximal and distal ends 192, 191 of the balloon 190 such that the radial channels 197A, 197B are located at a common longitudinal location. However, this is not meant to be limiting. The radial channels 197A, 197B may be located at separate longitudinal locations, such as one distal of the other such that inflation fluid is distributed to proximal and distal locations of the balloon 190 simultaneously. In other embodiments, multiple radial channels may be located along the length of the second member 166 between the distal and proximal ends 191, 192 of the balloon 190.

The U-turn manifold 170, as shown in FIGS. 6, 8A, and 8F-8K, connects the first member 163 and the second member 166 of the delivery device 160. In the embodiment shown, the U-turn manifold is oblong in cross-section including a distal end 171, a proximal end 172, an outer surface 178, a first lumen 173, a second lumen 175, and an opening 179 fluidly coupling the first and second lumens 173, 175. In an embodiment, the longitudinal length of the U-turn manifold 170, from the distal end 171 to the proximal end 172, can range from about 0.50 inch to 1 inch.

Figure 8G:
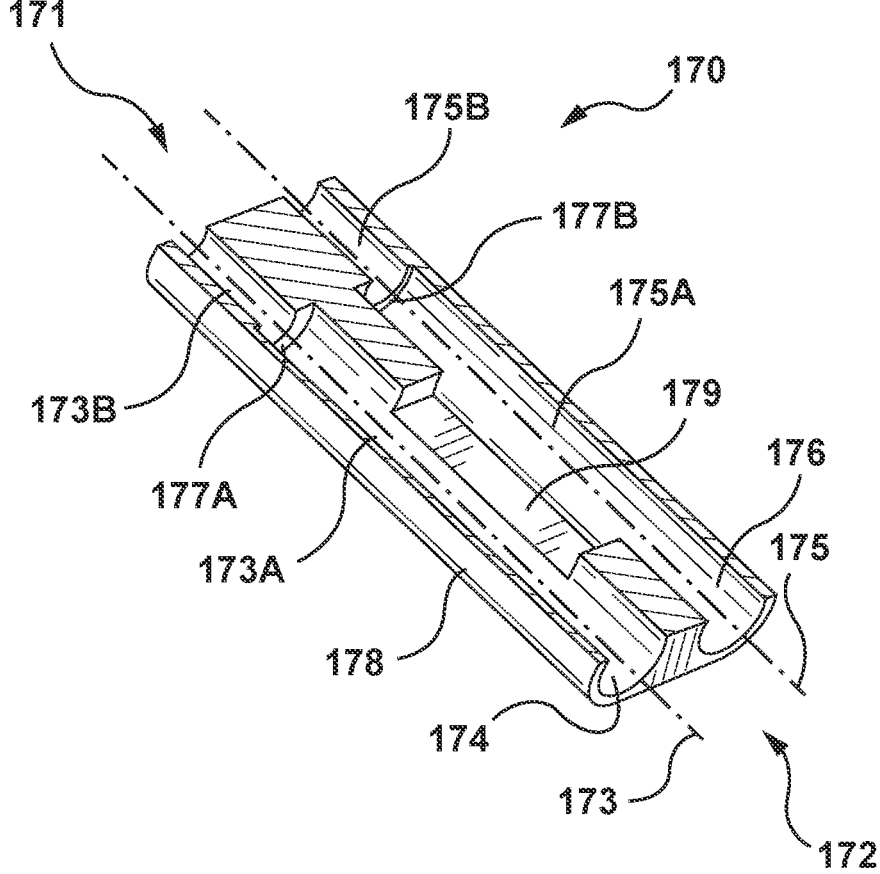
FIG. 8G shows a longitudinal cross-section of the U-turn manifold taken along line 8G-8G of FIG. 8F according to embodiments hereof

The first lumen 173 is configured to receive the distal portion of the first member 163 and a portion of the stylet 140 (described below) therein. The first lumen 173 is defined by a first inner surface 174 of the U-turn manifold 170 and extends through an entire longitudinal length of the U-turn manifold 170, from the distal end 171 to the proximal end 172. A shoulder or lip 177A is disposed between a proximal portion 173A and a distal portion 173B of the first lumen 173. The distal portion 173B of the first lumen 173 has a smaller inner diameter than the proximal portion 173A, as shown in FIG. 8G. The proximal portion 173A of the first lumen 173 is configured to fixedly receive the distal portion of the first member 163 of the delivery device 160 and the distal portion 173B is configured to slidably receive a portion of the stylet 140 therein. In embodiments, the inner diameter of the distal portion 173B of the first lumen 173 may be in the range of about 0.05 inch to 0.20 inch and the inner diameter of the proximal portion 173A of the first lumen 173 may be in the range of about 0.01 inch to 0.05 inch.

Figure 8H:
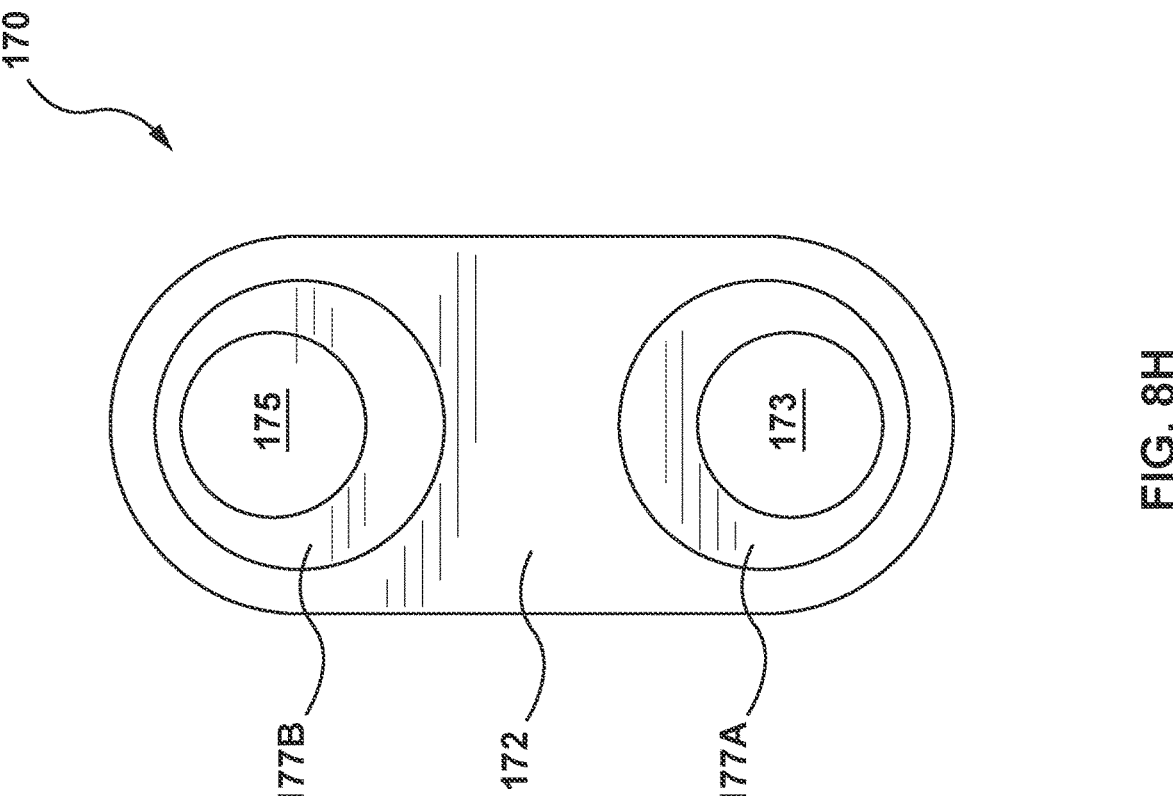
FIG. 8H shows a cross-section of the U-turn manifold taken along line 8H-8H of FIG. 8F according to embodiments hereof.

The second lumen 175 is configured to receive the distal portion of the second member 166 and a portion of the stylet 140 (described below) therein. The second lumen 175 is defined by a second inner surface 176 of the U-turn manifold 170 and extends through an entire longitudinal length of the U-turn manifold 170, from the distal end 171 to the proximal end 172. A shoulder or lip 177B is disposed between a proximal portion 175A and a distal portion 175B of the second lumen 175. The distal portion 173B of the second lumen 175 has a smaller inner diameter than the proximal portion 175A, as shown in FIGS. 8G and 8H. The proximal portion 175A of the second lumen 175 is configured to fixedly receive the distal portion of the second member 166 of the delivery device 160 and the distal portion 175B is configured to slidably receive a portion of the stylet 140 therein. In embodiments, the inner diameter of the distal portion 175B of the second lumen 175 may be in the range of about 0.05 inch to 0.20 inch and the inner diameter of the proximal portion 175A of the second lumen 175 may be in the range of about 0.01 inch to 0.05 inch.

Figures 8I, 8J:
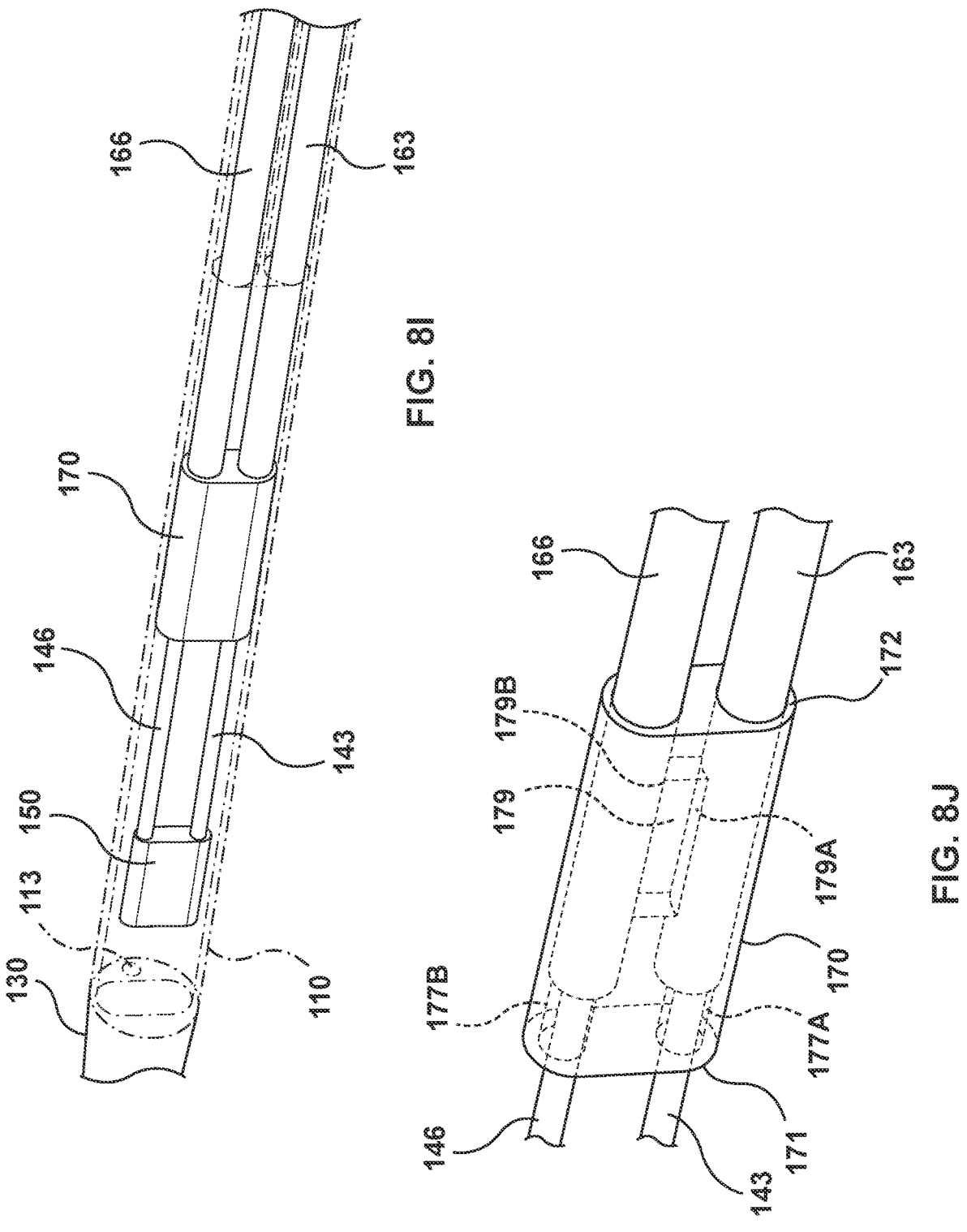
FIGS. 8I-8K show perspective views of the delivery device within the delivery system of FIG. 6 according to embodiments hereof.
Figure 8K:
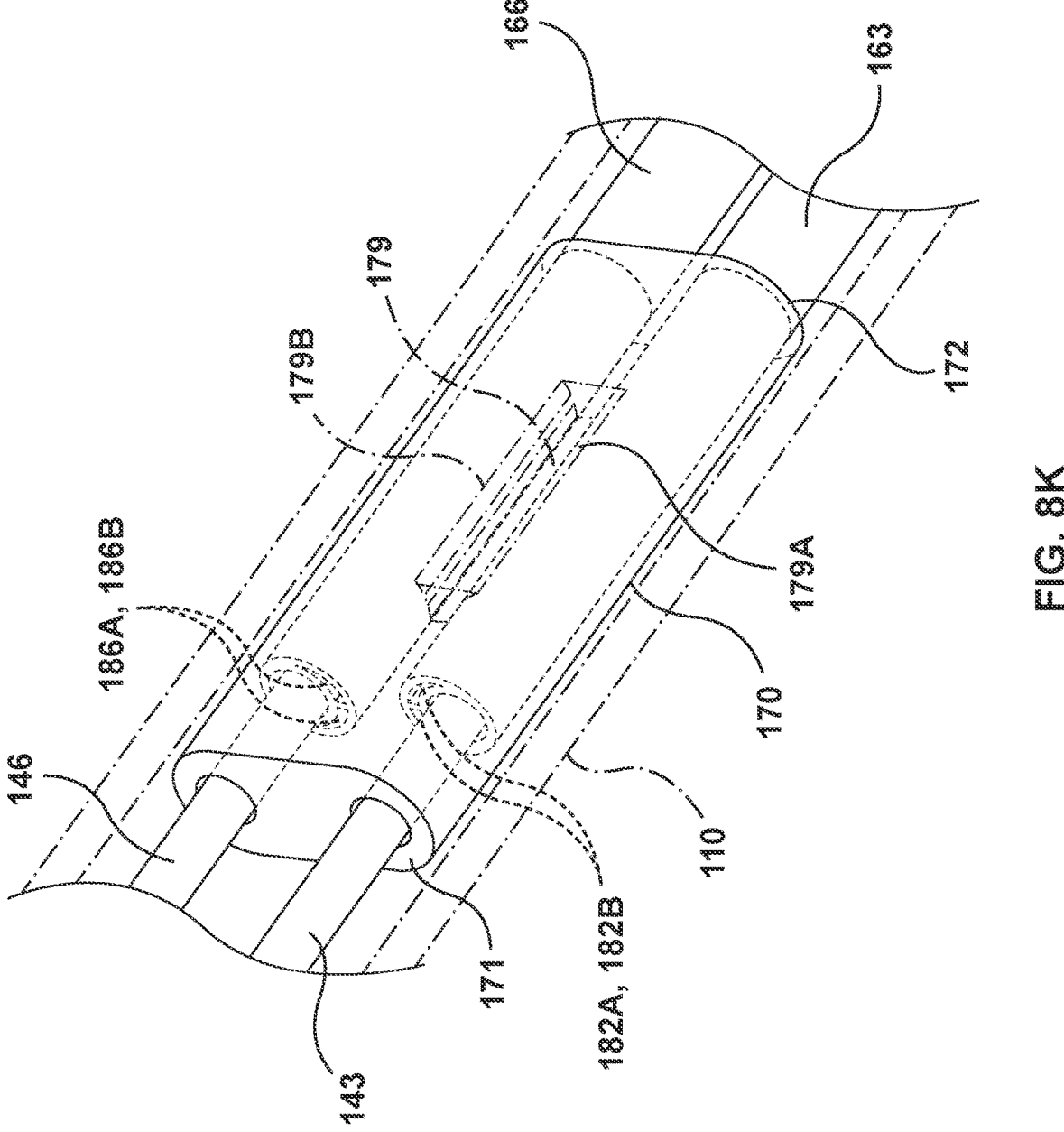

The opening 179 of the U-turn manifold 170 fluidly connects the first lumen 173 to the second lumen 175, as shown in FIG. 8G and 8I-8K. In the embodiment shown, the opening 179 is disposed proximal to the first and second shoulders 177A, 177B and distal to the proximal end 172 of the U-turn manifold 170. The opening 179 also connects the outer lumen 182 (with portions 182A, 182B) of the first member 163 and the outer lumen 186 (with portions 186A, 186B) of the second member 166. To achieve this connection, the first member 163 of the stent delivery device 160 includes a first cut-out or opening 179A that extends through the outer surface 180 of the first member 163 to the outer lumens 182A, 182B, as best shown in FIG. 8J. The first cut-out 179A of the first member 163 is sized and positioned to align with the opening 179 of the U-turn manifold 170 when the first member 163 is fixedly attached within the first lumen 173 of the U-turn manifold 170. Similarly, the second member 166 of the stent delivery device 160 includes a second cut-out or opening 179B that extends through the outer surface 184 of the second member 166 to the outer lumens 186A, 186B, as best shown in FIG. 8K. The second cut-out 179B of the second member 166 is sized and positioned to align with the opening 179 of the U-turn manifold 170 when the second member 166 is fixedly attached within the second lumen 175 of the U-turn manifold 170. Thus, the outer lumens 182A, 182B of the first member 163 are in fluid communication with the outer lumens 186A, 186B of the second member 166 of the stent delivery device 160. In embodiments, the opening 179 has a length of about 0.1 inch to 0.5 inch, a width of about 0.02 inch to 0.10 inch, and a height of about 0.02 inch to 0.20 inch.

Figure 7A:
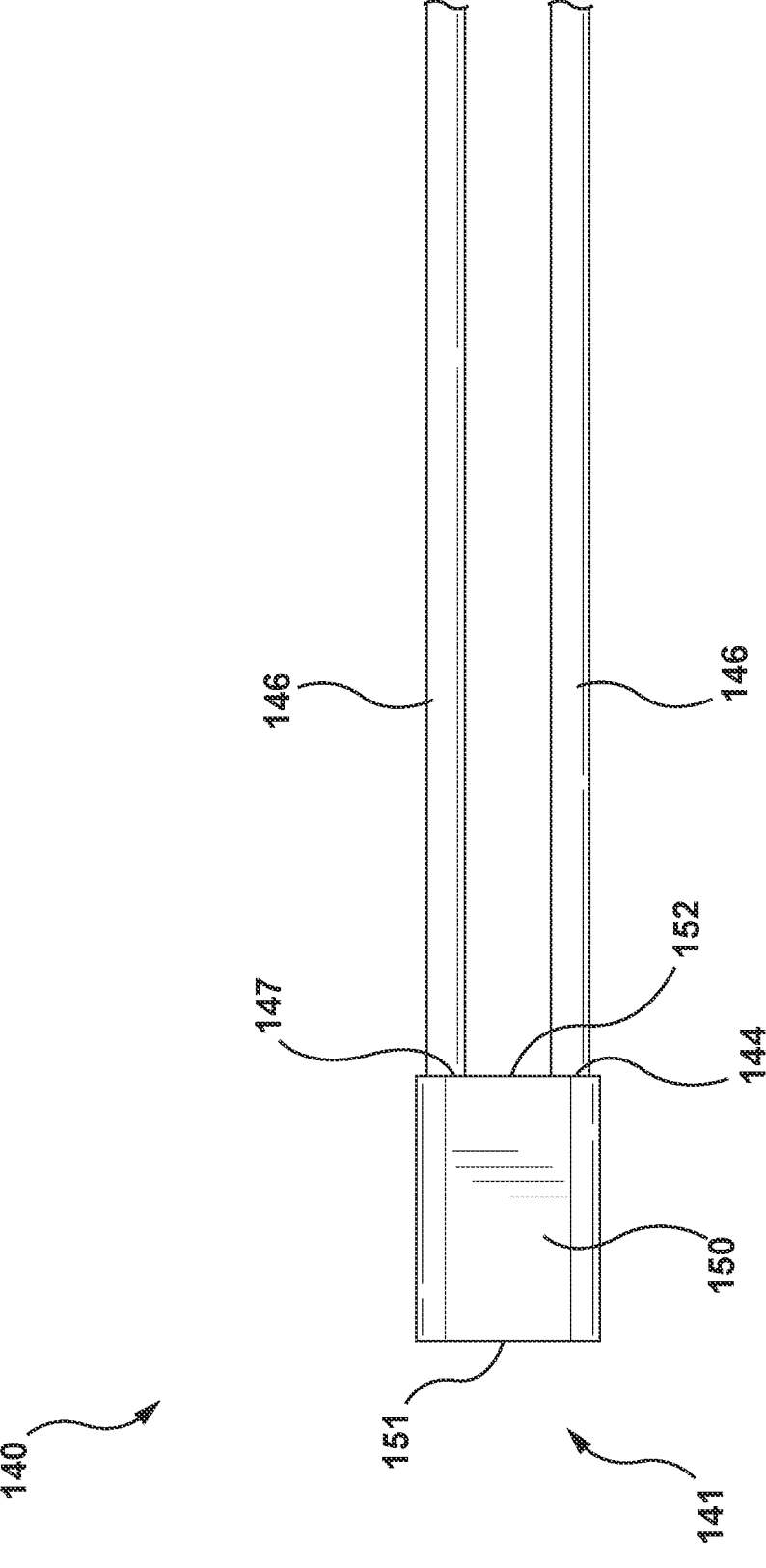
FIG. 7A shows a side view of a stylet of the delivery system of FIG. 6 according to embodiments hereof.
Figures 7B, 7C, 7D:
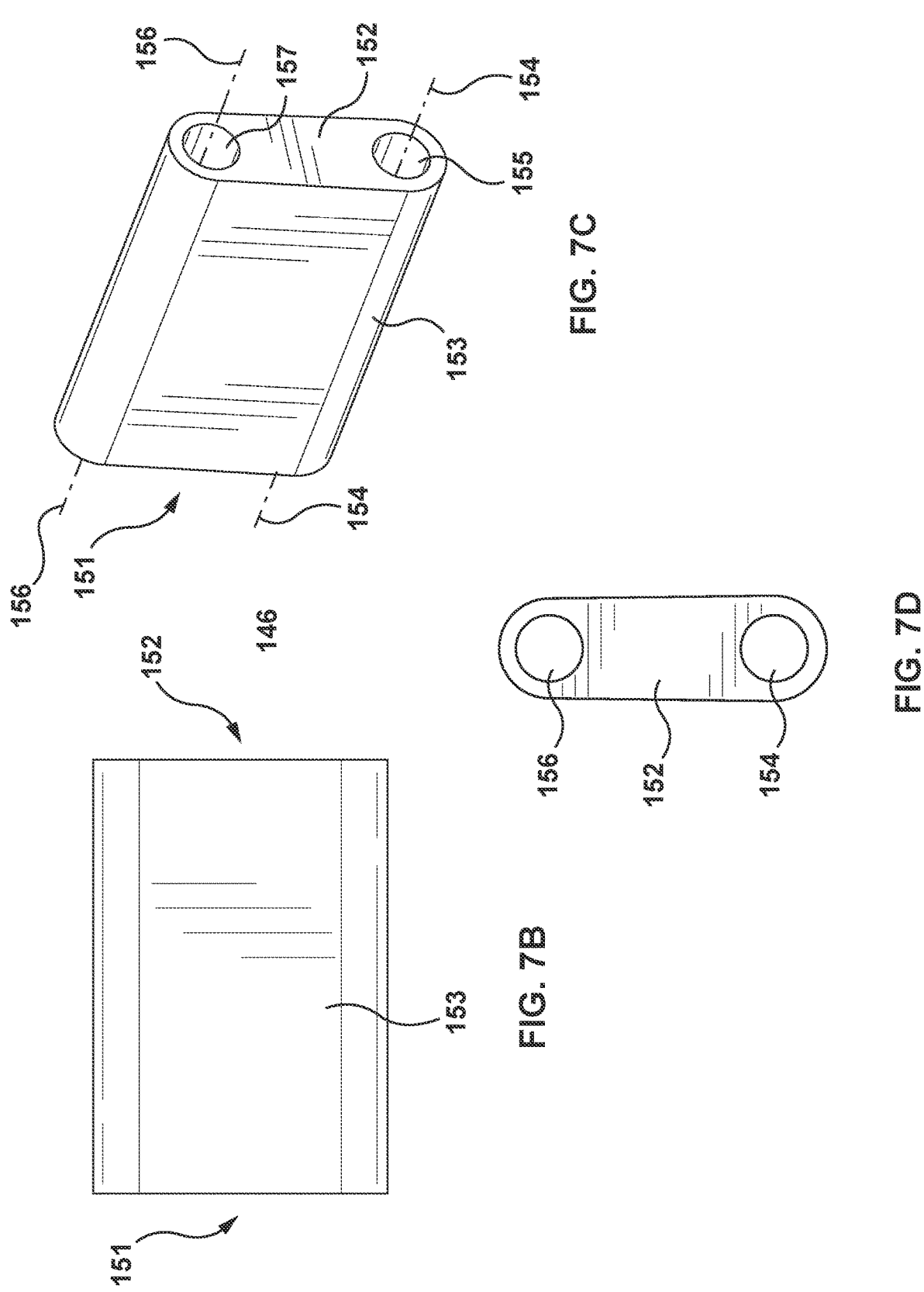
FIG. 7B shows a side view of a rigid structure of the stylet of FIG. 7A according to embodiments hereof.
FIG. 7C shows a perspective view of the rigid structure of FIG. 7B according to embodiments hereof.
FIG. 7D shows a cross section of the rigid structure of FIG. 7B according to embodiments hereof.
Figure 7E:
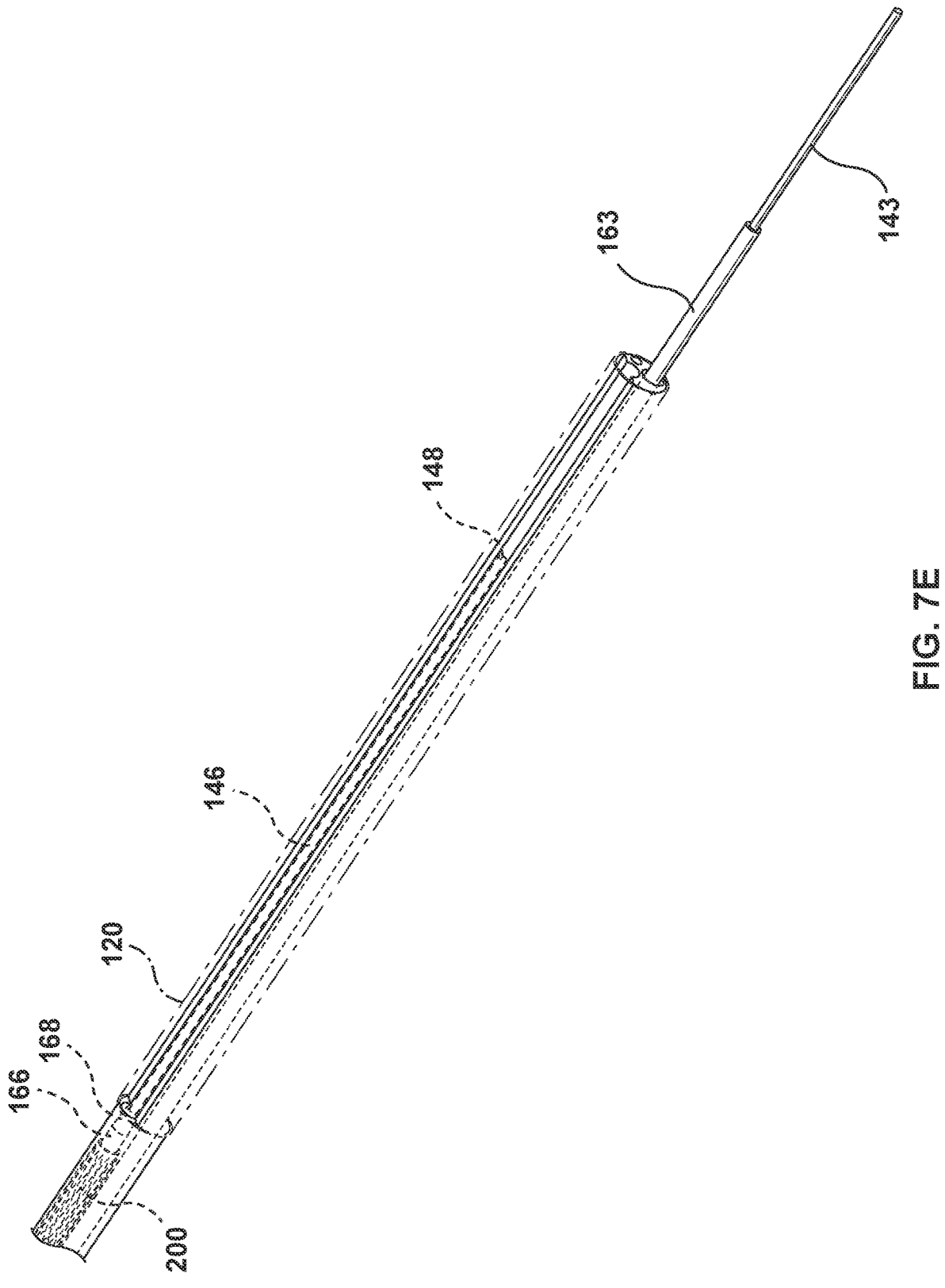
FIG. 7E shows a first member and a second member of the stylet of FIG. 7A within the delivery system according to embodiments hereof.

The stylet 140 of the delivery system 100, as shown in FIGS. 6, 7A and 7E, acts similar to a guidewire for the delivery device 160. The stylet 140 includes a distal end 141 and a proximal end (not shown). The stylet includes a first wire member 143, a second wire member 146, and a connector 150. The first wire member 143 is a longitudinal wire [Inventors—please confirm the first and second members of the stylet are guidewires] that includes a distal end 144 and a proximal end (not shown) that extends proximally outside of a patient in use. The second wire member 146 is a longitudinal wire member that includes a distal end 147 and a proximal end 148 (see FIG. 7E for proximal end 148). The first and second wire members 143, 146 are spaced or offset from each other such that the first and second wire members 143, 146 extend along different longitudinal axes. A longitudinal length of the first wire member 143 is longer than a longitudinal length of the second wire member 146 of the stylet 140, as shown in FIG. 6. The longitudinal length of the first wire member 143 can range from about 20 to 100 cm and the longitudinal length of the second wire member 146 can range from about 20 to 100 cm. The first wire member 143 and the second wire member 146 of the stylet 140 may have substantially circular cross-sections with a thickness or diameter of about 0.010 inch to 0.050 inch. The first wire member 143 and the second wire member 146 of the stylet 140 can comprise coiled wire, plastic overmolded solid core wire, plastic, nylon, polytetrafluoroethylene (PTFE) or any other materials known to those skilled in the art.

The connector 150 of the stylet 140 connects the first wire member 143 to the second wire member 146 such that movement of the first wire member 143 is transferred to the second wire member 146. The connector 150 may be oblong is cross-section and include a distal end 151, a proximal end 152, an outer surface 153, a first lumen 154, and a second lumen 156. A longitudinal length of the connector 150, from the distal end 151 to the proximal end 152, may be about 0.02 inch-0.25 inch. The first lumen 154 and the second lumen 156 may extend through an entire longitudinal length of the connector 150, but need not. The first lumen 154 is configured to fixedly receive the first wire member and the second lumen 156 is configured to fixedly receive the second wire member 146. The first lumen 154 and the second lumen 156 are spaced or offset from each other such that the first lumen 154 ad the second lumen 156 extend along different longitudinal axes and such that the first and second wire members 143, 146 align with the first and second central lumens 169A, 169B of the first and second members 163, 166, respectively. In an embodiment, such a spacing may be in the range of 0.02 inch to 0.25 inch. The connector 150 may be a crimp connector or other similar structure known to those skill in the art. The connector 150 may comprise metal and/or plastic materials, and/or any other materials known to those skilled in the art. The connector 150 may be coupled to the first and second wire members 163, 166 via crimping, overmolding, adhesives, and/or other coupling means.

The first lumen 154 is defined by a first inner surface 155 of the connector 150 and the second lumen 156 is defined by a second inner surface 157 of the connector 150, as shown in FIG. 7C. Both first and second lumens 154, 156 of the connector 150 may have a substantially circular cross-section, but may have a cross-section to match the shape of the first and second wire members 143, 146. As shown in FIGS. 7C-7D, the first lumen 154 and the second lumen 156 are spaced or offset from one another. In the orientation shown in FIGS. 7C-7D, the first lumen 154 is disposed directly below the second lumen 156 of the connector 150, but the orientation could be described as side-by-side depending on the orientation of the overall delivery system 100. As noted above, the first and second lumens 154, 156 are sized and shaped to receive the distal portions of the first and second wire members 143, 146 therein, respectively. The first lumen 154 and the second lumen 156 of the rigid structure 150 are equal in size. In embodiments, the first and second lumens 154, 156 may have a diameter that can range from about 0.01 inch to 0.05 inch. As described in more detail below regarding the method, once assembled, the connector 150 and the first and second wire members 143, 146 act as a single unit or piece. In other embodiments, the connector 150 and the first and second wire members 143, 146 may be a single piece.

A stent graft 200 that is to be deployed within the vasculature of the patient, which will be described in further detail below, is loaded onto the outer surface 193 of the balloon 190 disposed on a proximal portion of the second member 166 of the stent delivery device 160, as shown in FIG. 2. The stent graft 200 is crimped onto the outer surface 193 of the balloon 190 such that an inner surface of the stent graft 200 contacts the outer surface 193 of the balloon 190. In the embodiment shown, the stent graft 200 is balloon-expandable, which is described in further detail below. However this is not meant to be limiting, as the stent 200 may be any type of self-expandable, mechanically-expandable or balloon-expandable stent. If the stent graft is self-expanding, then the balloon 190 may be omitted and a retractable cover or other constraining mechanism (e.g., diameter reducing ties) may be used to restrain the stent graft and then release it at the appropriate time.

In an example of assembling the stent delivery device 160, the distal end 164 of the first member 163 is introduced to the first lumen 173 of the U-turn manifold 170 at its proximal end 172 and advanced distally within the first lumen 173 of the U-turn manifold 170 until the distal end 164 of the first member 163 abuts the first shoulder 177A within the first lumen 173 of the U-turn manifold 170, as best shown in FIG. 8K. The distal portion of the first member 163 is fixedly attached within the first lumen 173. The first shoulder 177A may block or close off the first and second portions 182A, 182B of the outer lumen 182 of the first member 163 such that fluid introduced to the outer lumen 182 cannot flow through the distal end 164 of the first member 163, or the first and second portions 182A, 182B may only extend distally within the first member to a location adjacent the opening 179 of the U-turn manifold 170. Similarly, the distal end 167 of the second member 166 of the stent delivery device 160 is introduced to the second lumen 175 of the U-turn manifold 170 at its proximal end 172. The second member 166 is then advanced distally within the second lumen 175 of the U-turn manifold 170 until the distal end 167 of the second member 166 abuts the second shoulder 177B within the second lumen 175 of the U-turn manifold 170, as best shown in FIG. 8K. The distal portion of the second member 166 is fixedly attached within the second lumen 175. The second shoulder 177B may block or close off the first and second portions 186A, 186B of the outer lumen 186 of the second member 166 such that fluid introduced to the outer lumen 186 cannot flow through the distal end 167 of the first member 166, or the first and second portions 186A, 186B may only extend distally within the second member 166 to a location adjacent the opening 179 of the U-turn manifold 170. In the assembled configuration, the first member 163 and the second member 166 of the stent delivery device 160 extend proximally from the U-turn manifold 170 and extend parallel to one another. The stent graft 200 is loaded onto the outer surface 193 of the balloon 190 disposed on the proximal portion of the second member 166 of the stent delivery device 160.

Figure 9:
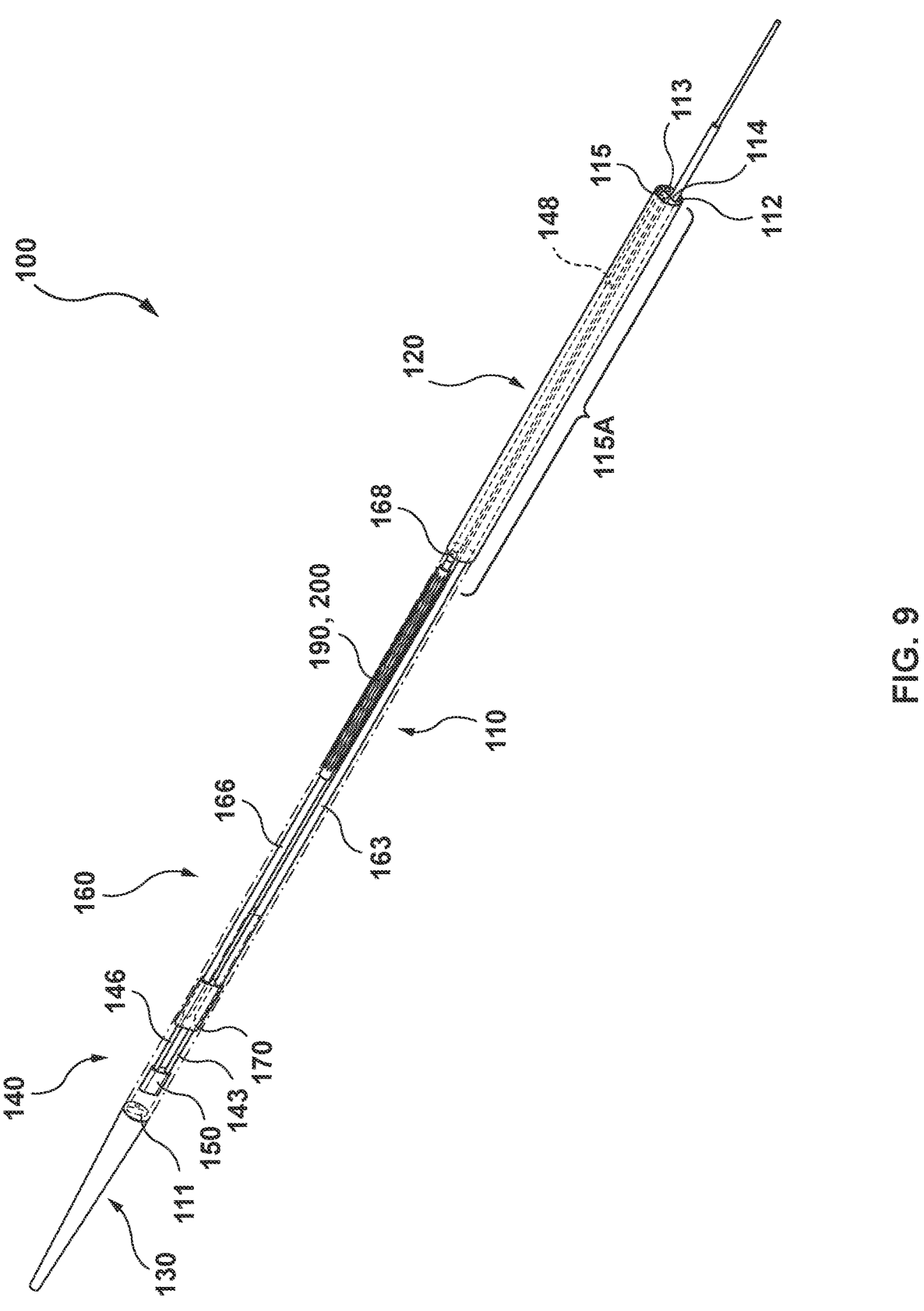
FIG. 9 shows a perspective view of the delivery device according to embodiments hereof.

FIG. 9 shows the distal portion of a fully assembled system 100 in a covered configuration according to embodiments herein. As explained above, the first member 163 of the delivery device 160, the first wire member 143 of the stylet 140, the shaft 110, and the cover 120 all extend proximally to or through a handle (not shown) of the delivery system 100. The delivery device 160 is disposed within the delivery system 100 such that the first member 163 extends through the first main lumen 114 of the shaft 110 and the second member 166 extends through the second main lumen 115 of the shaft 110 of the delivery system 100, as shown in FIG. 9. The U-turn manifold 170 is disposed within the U-turn portion 117 of the shaft 110. Further, the first wire member 143 of the stylet 140 extends through the first lumen 173 of the U-turn manifold 170 and the first central lumen 169A of the first member 163 of the stent delivery device 160 that is disposed within the first main lumen 114 of the shaft 110. The second wire member 146 of the stylet 140 extends through the second lumen 175 of the U-turn manifold 170 and the second central lumen 169B of the second member 166 of the stent delivery device 160 that is disposed within the second main lumen 115 of the shaft 110. The connector 150 of the stylet 140 is slidably disposed within the U-turn portion 117 of the shaft 110. In this assembled configuration, the connector 150 of the stylet 140 is disposed distal to the U-turn manifold 170 of the delivery device 160, as can be seen in FIG. 9. Both the connector 150 and the U-turn manifold 170 can slidably move distally or proximally within the U-turn portion 117 of the shaft 110, as shown in FIGS. 7F-7G.

Figures 7F, 7G:
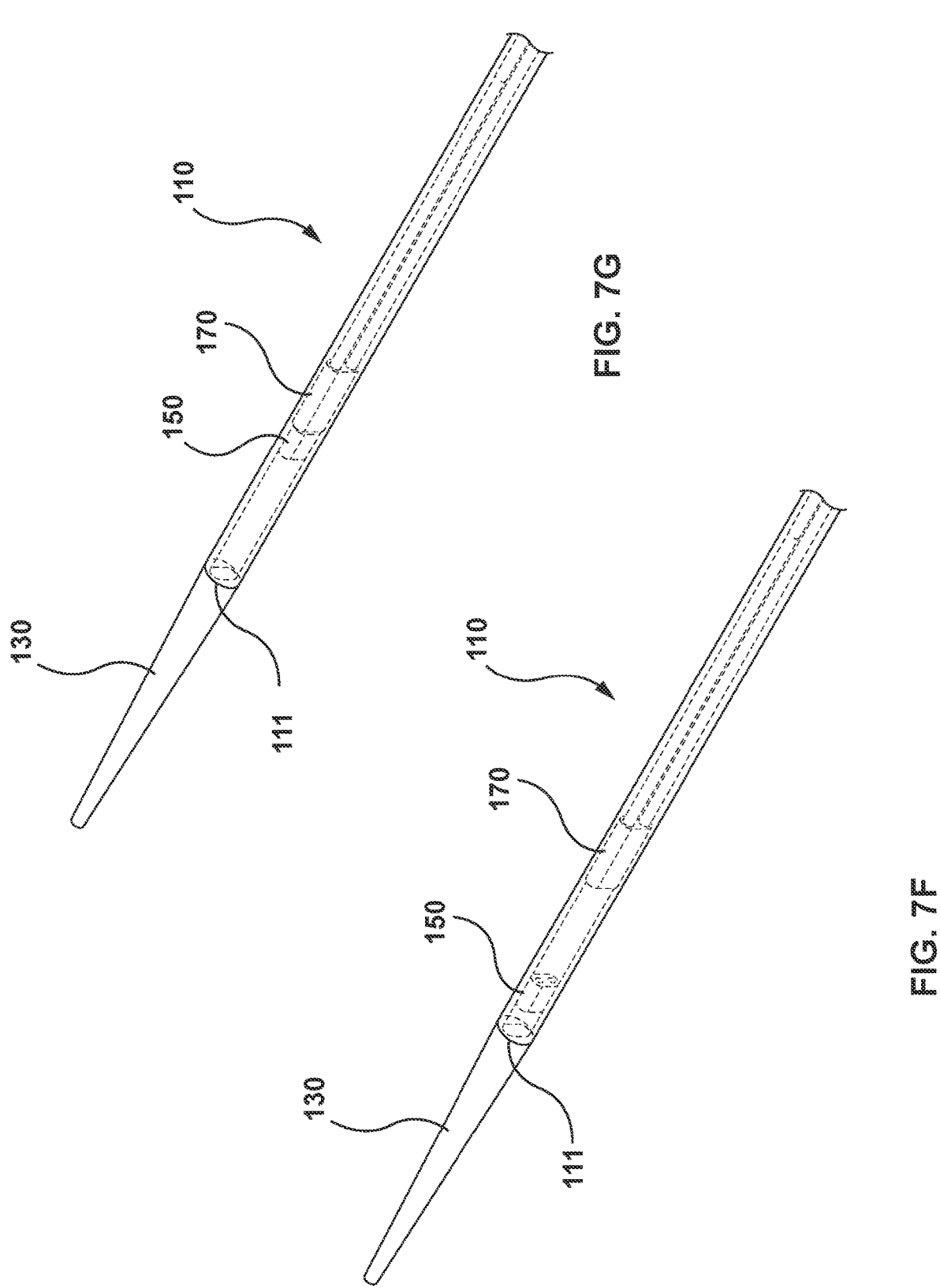
FIGS. 7F-7G show the rigid member of the stylet of FIG. 7A within the delivery system according to embodiments hereof.

FIG. 7F shows the connector 150 and the U-turn manifold 170 disposed at the distal end 111 of the shaft 110 of the delivery system 100 and FIG. 7G shows the rigid member 150 and the U-turn manifold 170 displaced proximally from the distal end 111 of the shaft 110 of the delivery system 100.

With the stylet 140 disposed at the distal end of the shaft 110 of the delivery system 100, the proximal end 148 of the second wire member 146 of the stylet 140 terminates within the skived portion 115A of the second main lumen 115, as can be seen in FIGS. 7E and 9. With the stent delivery device 160 disposed at the distal end of the shaft 110, the proximal end 168 of the second member 166 terminates just distal to the skived portion 115A of the second main lumen 115 of the shaft 110, as shown in FIGS. 7E and 9, but may instead terminate within the skived portion 115A. As shown in FIGS. 7E and 9, the proximal end 148 of the second wire member 146 of the stylet 140 extends proximally past the proximal end 168 of the second member 166 of the stent delivery device 160. In this covered or delivery configuration, the cover 120 of the delivery system 100 is disposed over slid the skived portion 115A of the second main lumen 115 such that the second wire member 146 is enclosed by the cover 120, as shown in FIGS. 7E and 9. If a portion of the second member 166 is disposed within the skived portion 115A in the delivery configuration, then the cover 120 would also enclose the second member 166 within the second main lumen 115 at the skived portion 115A. The tip 130 of the delivery system 100 is coupled to the distal end 111 of the shaft 110 of the delivery system 100 and extends distally therefrom, as shown in FIG. 9.

FIG. 10 is a block diagram of a method 600 for delivering a stent graft 200 within a branch vessel, particularly an internal iliac artery 540 of a patient's vasculature 500 using the delivery system 100 described above after an iliac branch device (IBD) 300 is deployed within the corresponding common iliac artery 520 of the patient's vasculature 500. The stent graft 200 can be, for example, an internal iliac stent graft 200. The method described herein will be with respect to delivering an internal iliac stent graft 200 within an internal iliac artery 540 of a patient's vasculature 500, however, this is not meant to be limiting, as the delivery device 100 described herein can be used to deliver various types of stents that are to be deployed, for example, in a vessel that includes a bifurcation or highly angled vasculature that creates difficulty when deploying the stent within the vasculature.

Figure 11:
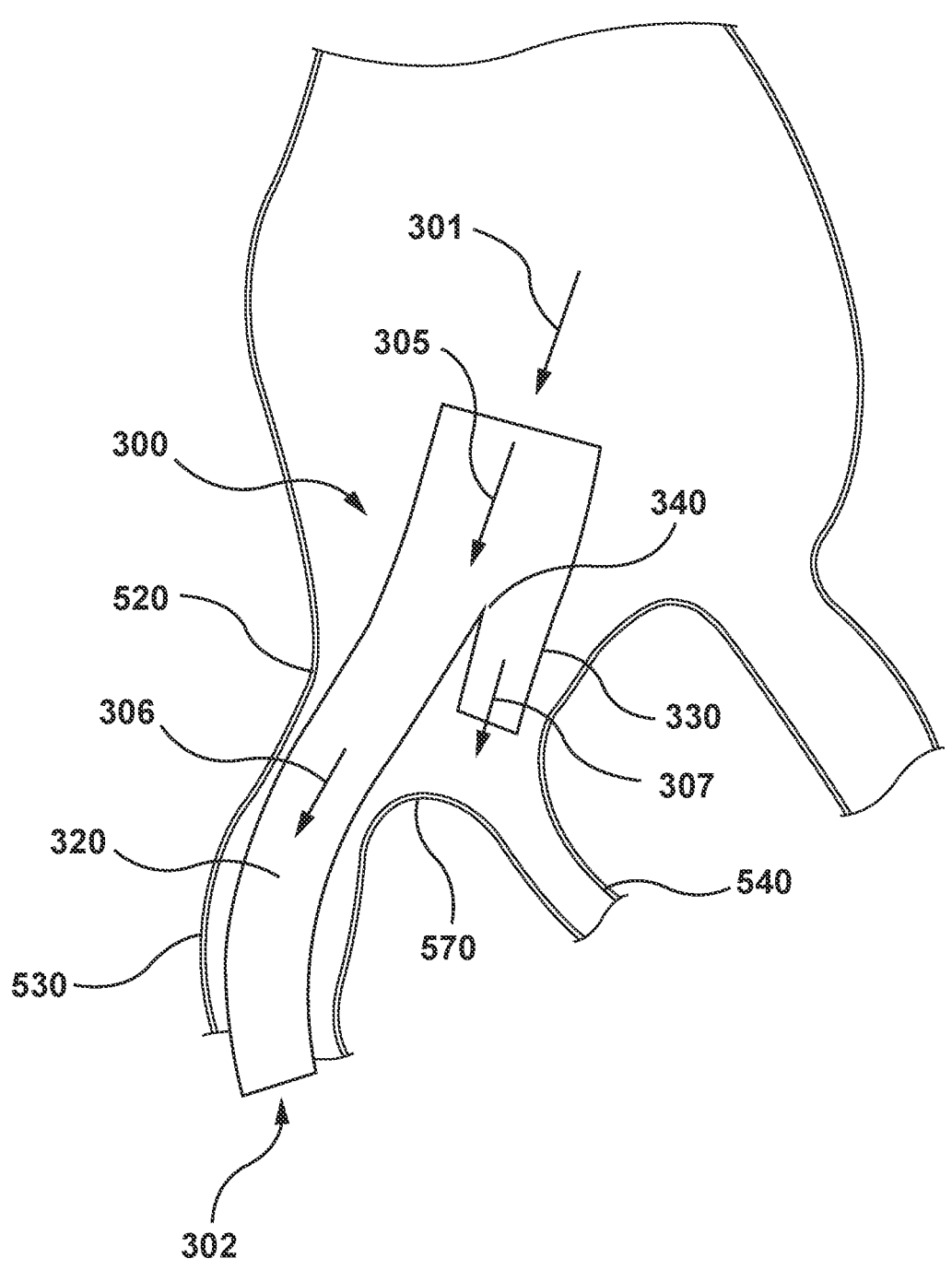
FIG. 11 shows a step in the method of FIG. 10, showing an internal branch device deployed within a patient's vasculature according to embodiments hereof.

In a first step 602 of the method 600, an iliac branch device 300 is deployed within a common iliac artery 520. An exemplary iliac branch device 300 disposed within the patient's vasculature 500 is shown in FIG. 11. The iliac branch device 300 is a stent graft that includes a first end 301, a second end 302, a first branch 320 and a second branch 330. The first end 301 of the iliac branch device 300 is a tubular stent structure that includes a central lumen 305 that branches or splits into the first branch 320 and the second branch 330 at a bifurcation 340 of the iliac branch stent graft 300. The first end 301 of the iliac branch device 300 is disposed within the common iliac artery 520 above the internal iliac artery 540, as shown in FIG. 11. The first branch 320 of the iliac branch device 300 defines a lumen 306 and extends down the external iliac artery 530 of the common iliac artery 520, as shown in FIG. 11. The second branch 330 of the iliac branch device 300 defines a separate lumen 307 and extends towards the internal iliac artery 540, but terminates before it enters the internal iliac artery 540, as can be seen in FIG. 11. The iliac branch device 300 may be delivered and deployed by devices and methods know to those skilled in the art. In an alternate embodiment, the iliac branch device may be a side-branching device instead of a bifurcating device, such that the central lumen 305 extends and becomes the first branch 320 and the second branch 330 extends from a sidewall thereof and towards the internal iliac artery 540. The disclosed delivery system for an internal iliac stent graft may be used with either of the above iliac branch devices, or any other such device with a branch or leg extending towards an internal iliac artery above the second bifurcation 570.

Figure 12:
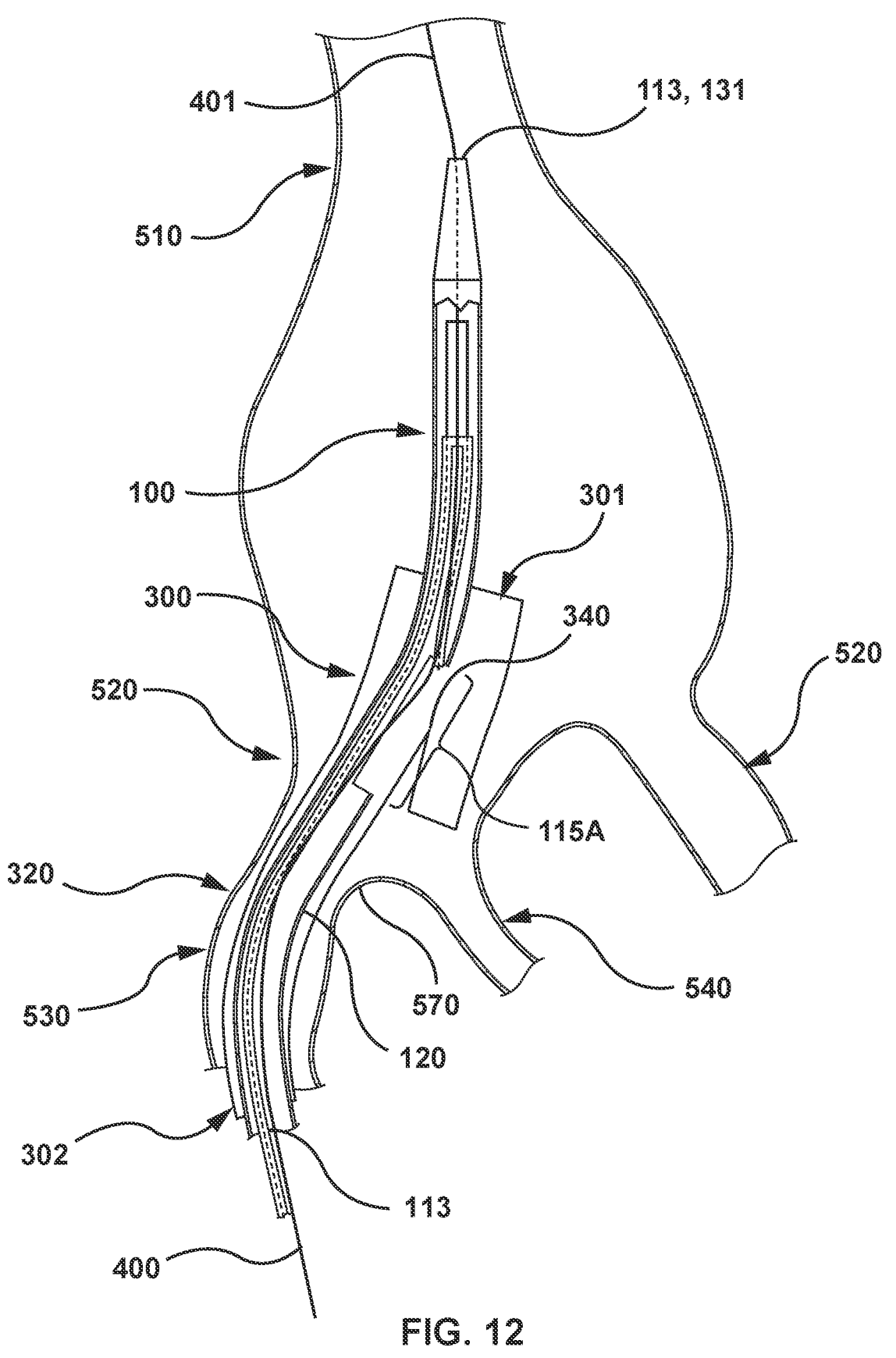
FIG. 12 shows a step in the method of FIG. 10, showing the delivery system being advanced through the internal branch device according to embodiments hereof.

In a second step 604 of the method 600, the delivery system 100 in the delivery configuration is inserted within the external iliac artery 530 of the vasculature 500 and is tracked towards the aorta 510 of the patient (in an upwards direction in FIG. 12), as shown in FIG. 12. In this step, a distal end 401 of a guidewire 400 may be inserted within the external iliac artery 530 and is tracked towards the aorta 510 of the patient, as shown in FIG. 12. The distal end 401 of the guidewire 400 enters the iliac branch device 300 from the second end 302, by entering the lumen 306 of the first branch 320 of the iliac branch device 300, and extends through the iliac branch device 300 until it exits through the main lumen 305 of the iliac branch device 300 at the first end 301, as shown in FIG. 12. A proximal end (not shown) of the guidewire 400, disposed outside of the vasculature 500 of the patient, is inserted into a distal end of the guidewire lumen 133 disposed at the distal end 131 of the tip 130 of the delivery system 100 and tracked through the guidewire lumen 133 and into the guidewire lumen 113, as described above. The guidewire 400 is advanced through the guidewire lumen 113 such that the guidewire 400 extends through the entire guidewire lumen 113 of the delivery system 100 and exits through a proximal end of the guidewire lumen 113 disposed at the proximal end of shaft 110. The delivery system 100 can then be introduced to the vasculature 500 of the patient and tracked over the guidewire 400 within the vasculature 500, as shown in FIG. 12.

In a step 606 of the method 600, the delivery system 100 is tracked over the guidewire 400 and enters the iliac branch device 300 through the lumen 306 the first branch 320 and is tracked upwards through the main lumen 305 of the iliac branch device 300 at the first end 301 until at least a portion of the skived portion 115A is disposed above both the bifurcation 340 of the iliac branch device 300 and the second bifurcation 570 of the vasculature 500, as shown in FIG. 12.

Figures 13A, 13B:
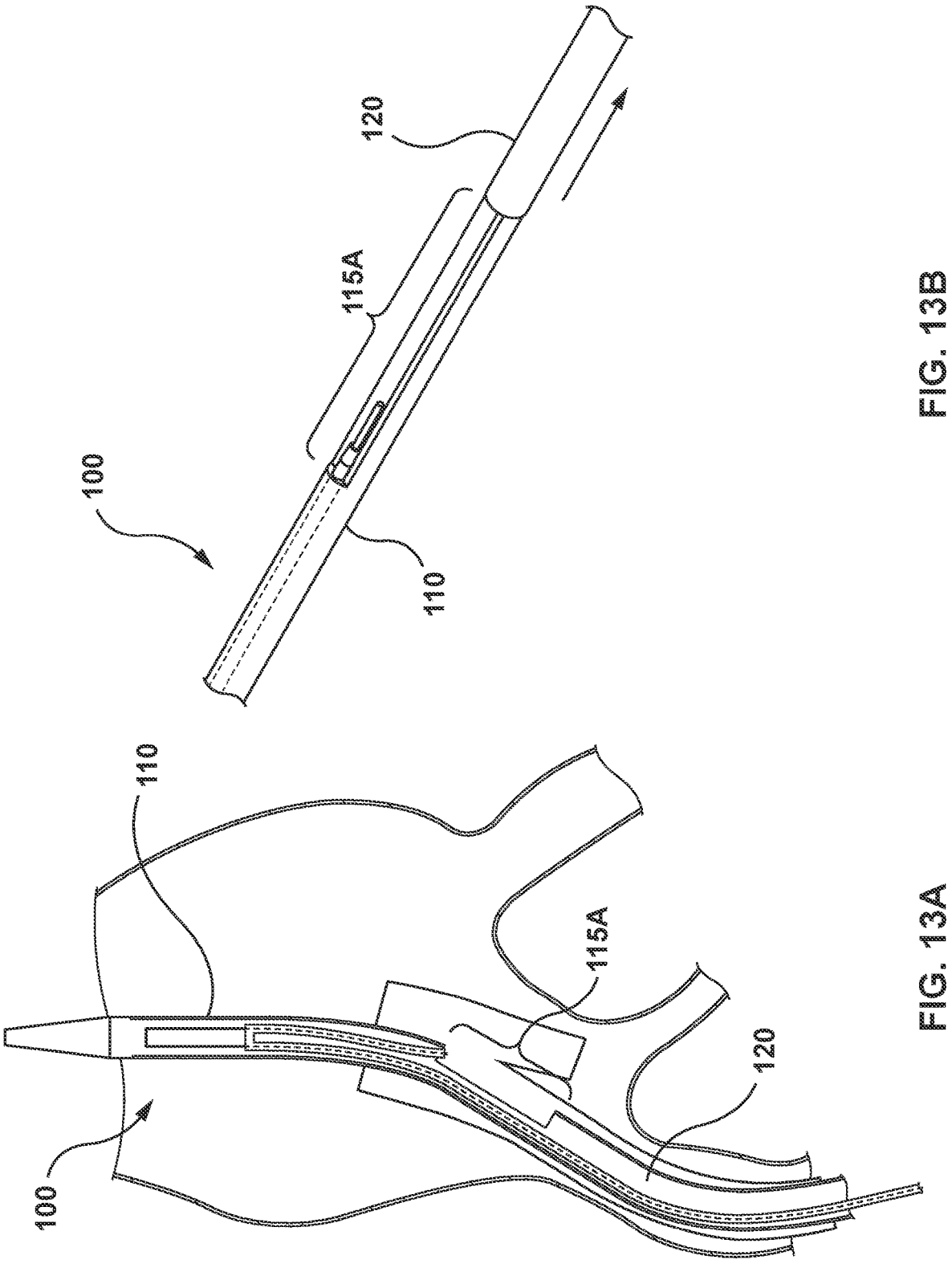
FIGS. 13A-13B show a step in the method of FIG. 10, showing the cover being retracted proximally from the delivery system according to embodiments hereof.
Figure 13D:
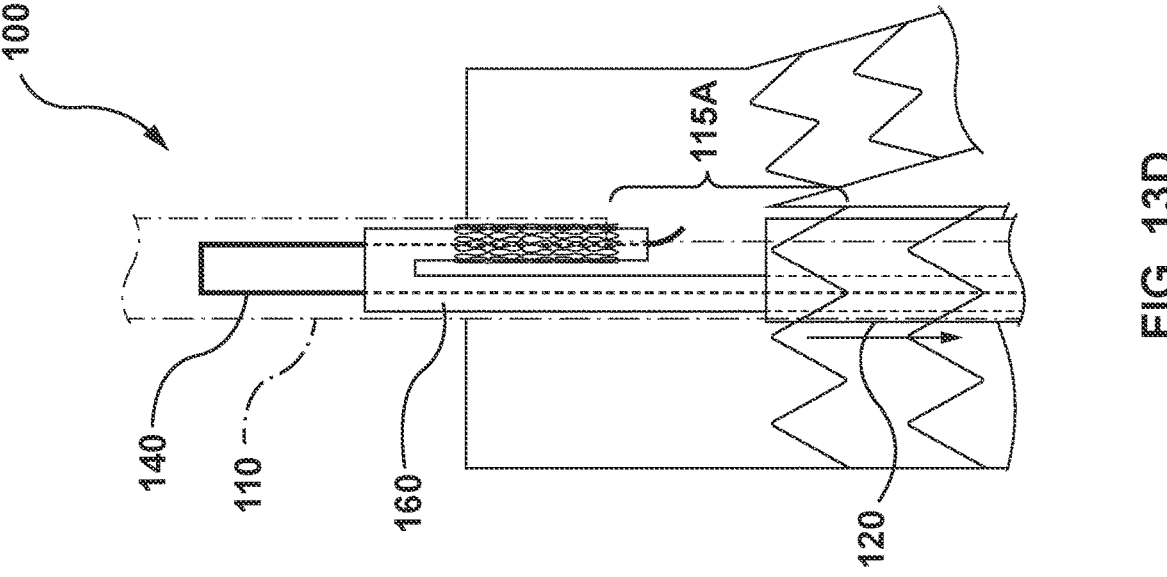
FIG. 13D shows the cover retracted proximally from the delivery system and exposing the skived portion of the shaft according to embodiments hereof.
Figure 13C:
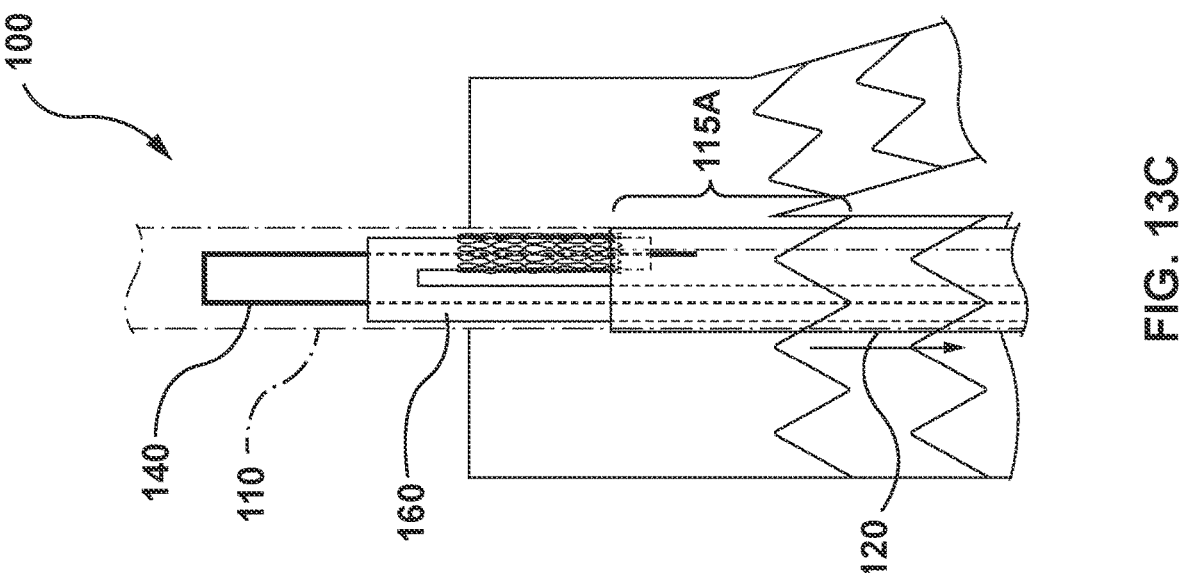
FIG. 13C shows the cover of the delivery system covering the skived portion of the shaft according to embodiments hereof.

In a step 608 of the method 600, the cover 120 of the delivery assembly 100 is pulled proximally to uncover the skived portion 115A of the shaft 110. Prior to sliding the cover 120 proximally relative to the delivery assembly 100, the cover 120 fully sheaths the skived portion 115A of the shaft 110 in the covered configuration, as shown in FIG. 13C. The cover 120 is pulled proximally (in FIG. 13D, in a downward direction), using an actuator attached to the handle of the delivery system 100, such that at least a distal portion of the skived portion 115A is exposed and is no longer covered by the cover 120 of the delivery assembly 100, as shown in FIG. 13D. As a result, the delivery assembly 100 transitions to an uncovered configuration where the skived portion 115A of the shaft 110 is exposed within the vasculature 500 of the patient, and more specifically within the iliac branch device 300, as shown in FIGS. 13A, 13B, and 13D.

Figure 14B:
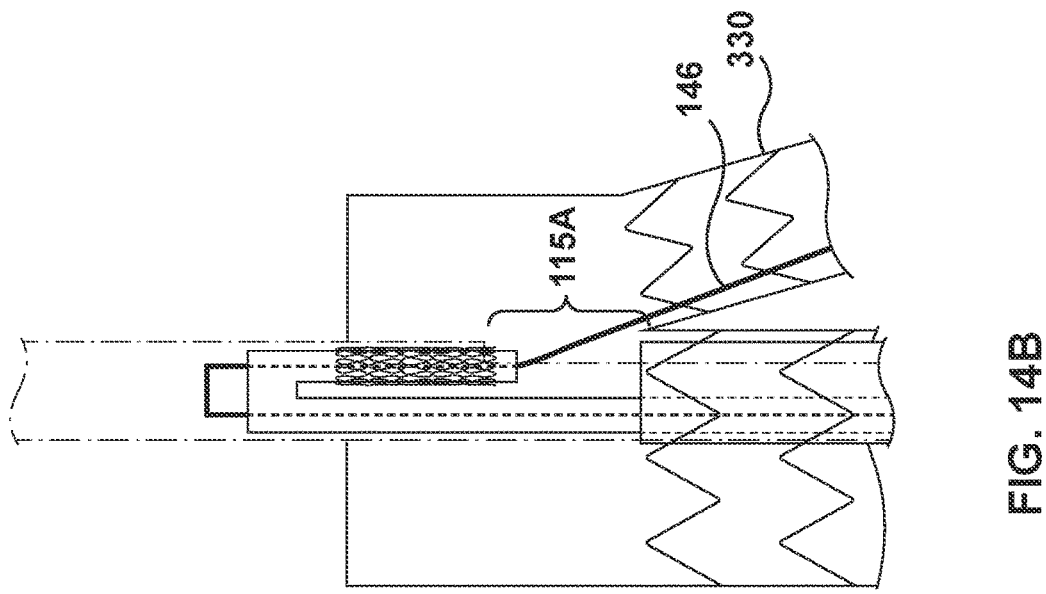
FIGS. 14A-14B show a step in the method of FIG. 10, showing the stylet being advanced within an internal iliac artery of a patient according to embodiments hereof.
Figure 14A:
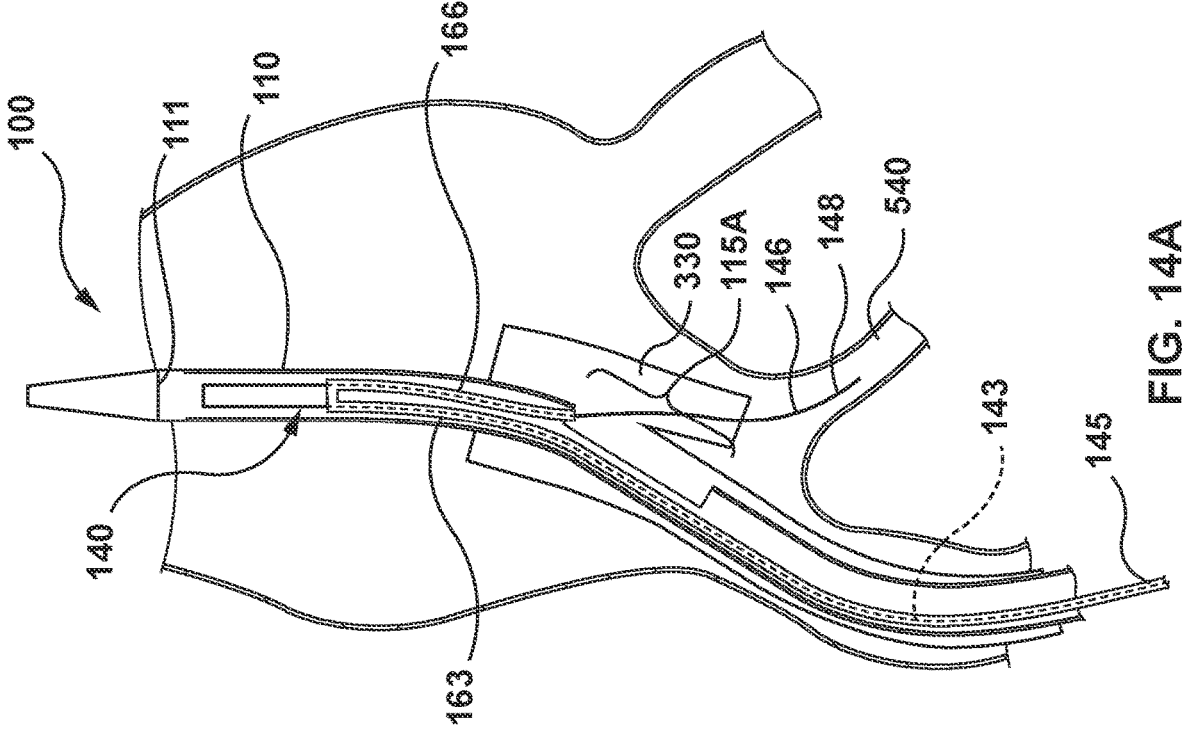

In a step 610 of the method 100, a user may pull the proximal end 145 of the first wire member 143 of the stylet 140 proximally relative to the shaft 110 of the delivery system 100. Prior to pulling the first wire member 143 of the stylet 140 proximally, the connector 150 of the stylet 140 is disposed within the U-turn portion 117 of the shaft 110 at its distal end 111, as shown in FIG. 7F. As the first wire member 143 is pulled proximally from the delivery system 100, the connector 150 disposed within the distal end 111 of the shaft 110 slides proximally within the U-turn portion 117 of the shaft 110, as shown in FIG. 7G. As the connector 150 slides proximally, the connector 150 moves the second wire member 146 of the stylet 140 proximally within the lumen 169B of the second member 166 of the delivery device 160 disposed in the second main lumen 115 of the shaft 110. As the stylet 140 is pulled proximally, the delivery device 160 within the shaft 110 of the delivery system 100 remains fixed and does not move. With the cover 120 retracted proximally, as the second wire member 146 is moved proximally, the second wire member 146 advances out of the skived portion 115A of the second main lumen 115, through the second branch 330 of the iliac branch device 300, and into the internal iliac artery 540, as shown in FIGS. 14A and 14B. As a result of this step, the proximal end 148 of the second member 146 of the stylet 140 is disposed within the internal iliac artery 540 of the patient.

In a step 612 of the method 600, the proximal end 165 of the first member 163 of the delivery device 160 is pulled proximally relative to the shaft 110 of the delivery system

Figures 15A, 15B:
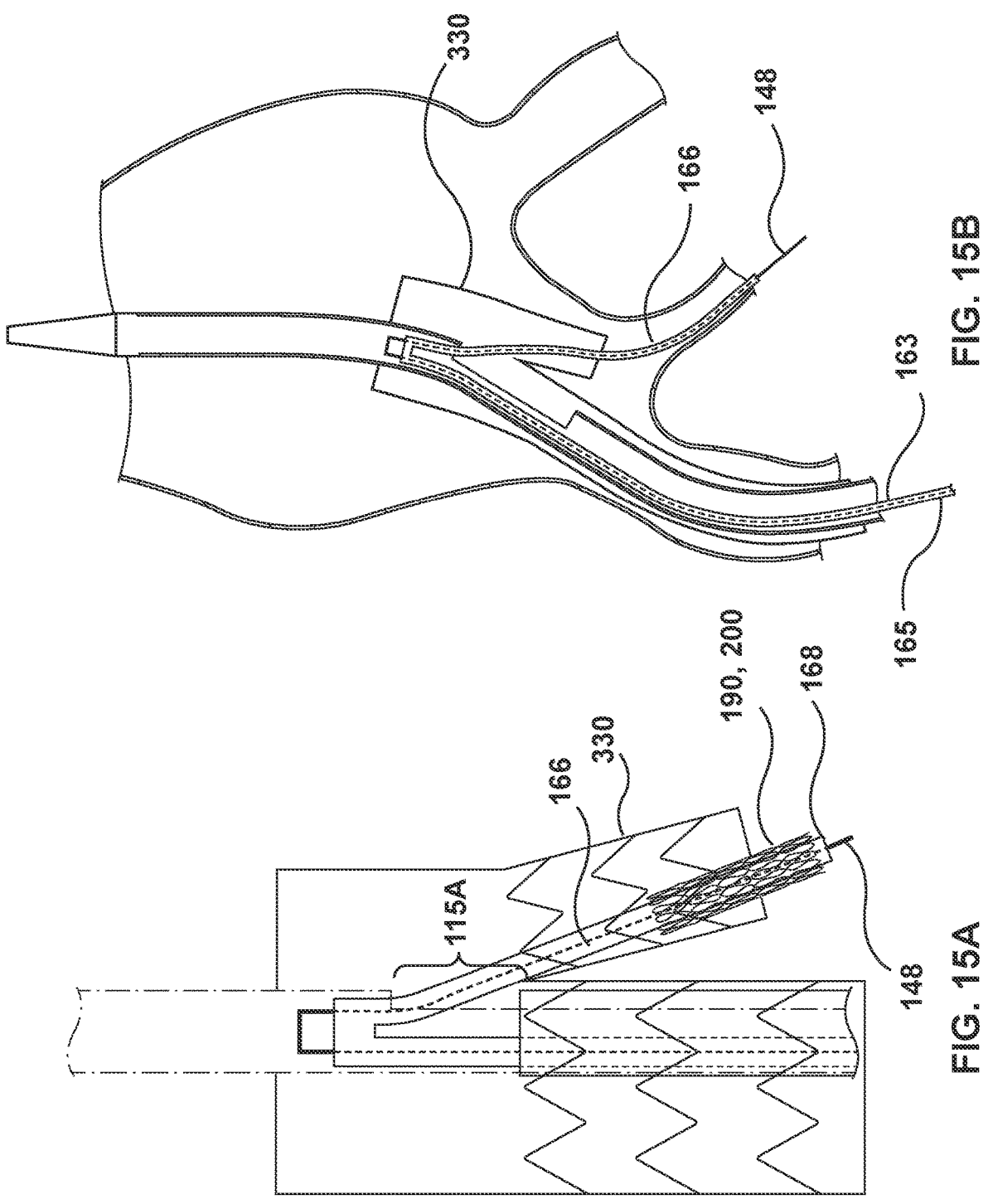
FIGS. 15A-15B show a step in the method of FIG. 10, showing the delivery device and the stent being advanced within the internal iliac artery of the patient according to embodiments hereof.

100. Prior to pulling the first member 163 of the delivery device 160, the U-turn manifold 170 of the delivery device 160 is disposed within the U-turn portion 117 of the shaft 110 proximal to the connector 150 of the stylet 140. As the first member 163 of the delivery device 160 is pulled proximally from the delivery system 100 by the user, the U-turn manifold 170, disposed within the U-turn portion 117 of the shaft 110, slides proximally within the shaft 110, as shown in FIGS. 15A-15B. As the U-turn manifold 170 slides proximally, the U-turn manifold 170 moves the second member 166 of the delivery system 160 proximally within the second main lumen 115 of the shaft 110 and over the second wire member 146 of the stylet 140. As the first member 163 of the delivery device 160 continues to be pulled proximally over the first wire member 143 of the stylet 140, the second member 166 of the delivery device 160 advances over the second wire member 146 of the stylet 140 and into the internal iliac artery 540. Thus, the second member 166 of the delivery device 160 exits through the skived portion 115A of the shaft 110 and advances through the second branch 330 of the iliac branch device 300 and enters the internal iliac artery 540 of the patient's vasculature 500, as shown in FIGS. 15A-15B. As shown in FIG. 15A, the internal iliac stent graft 200 is loaded on the balloon 190 that is coupled to the proximal end 168 of the second member 166 of the delivery device 160, and thus the balloon 190 and the iliac stent graft 200 are disposed within the internal iliac artery 540 in FIG. 15B.

Figure 16:
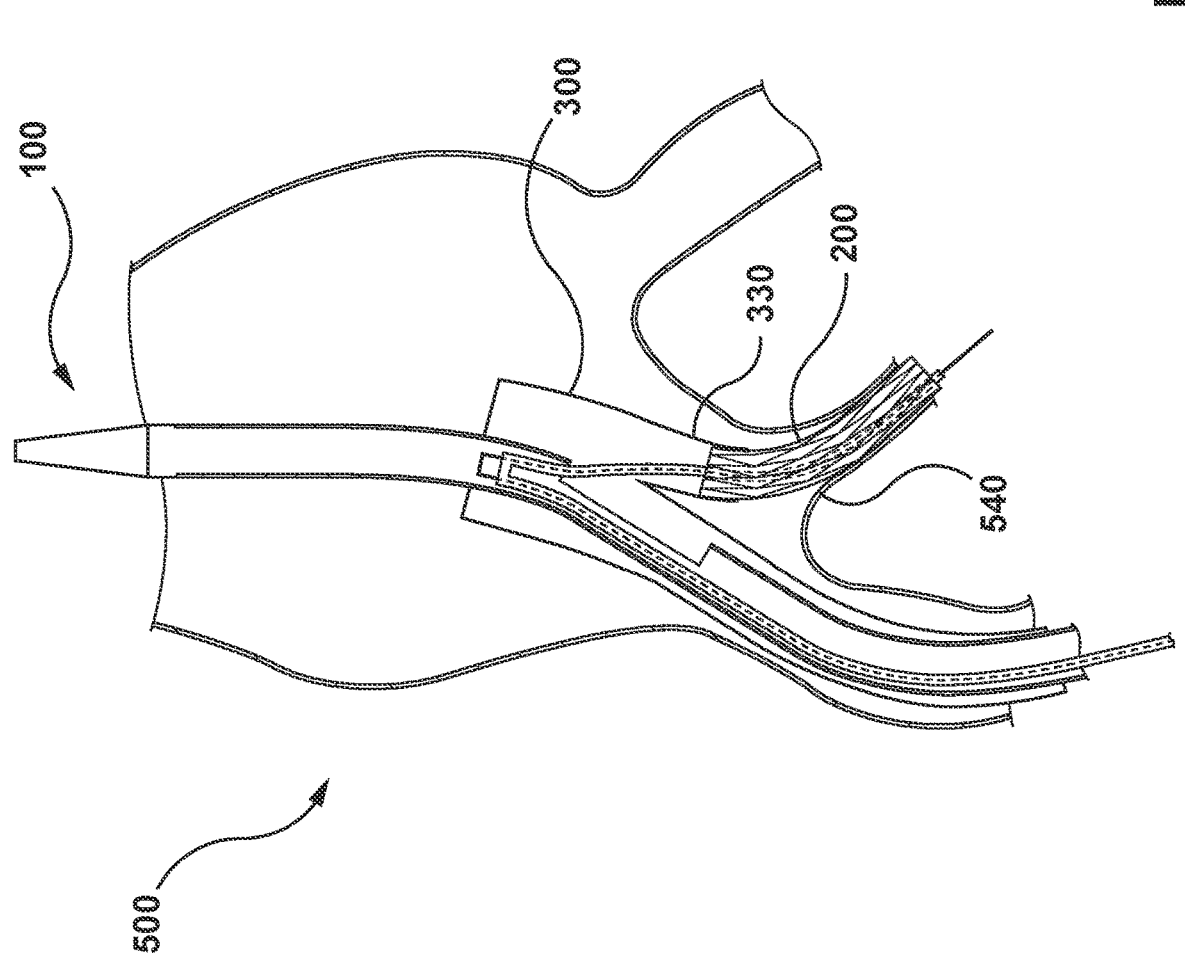
FIG. 16 shows a step in the method of FIG. 10, showing the stent being deployed within the internal iliac artery of the patient according to embodiments hereof.
Figure 17:
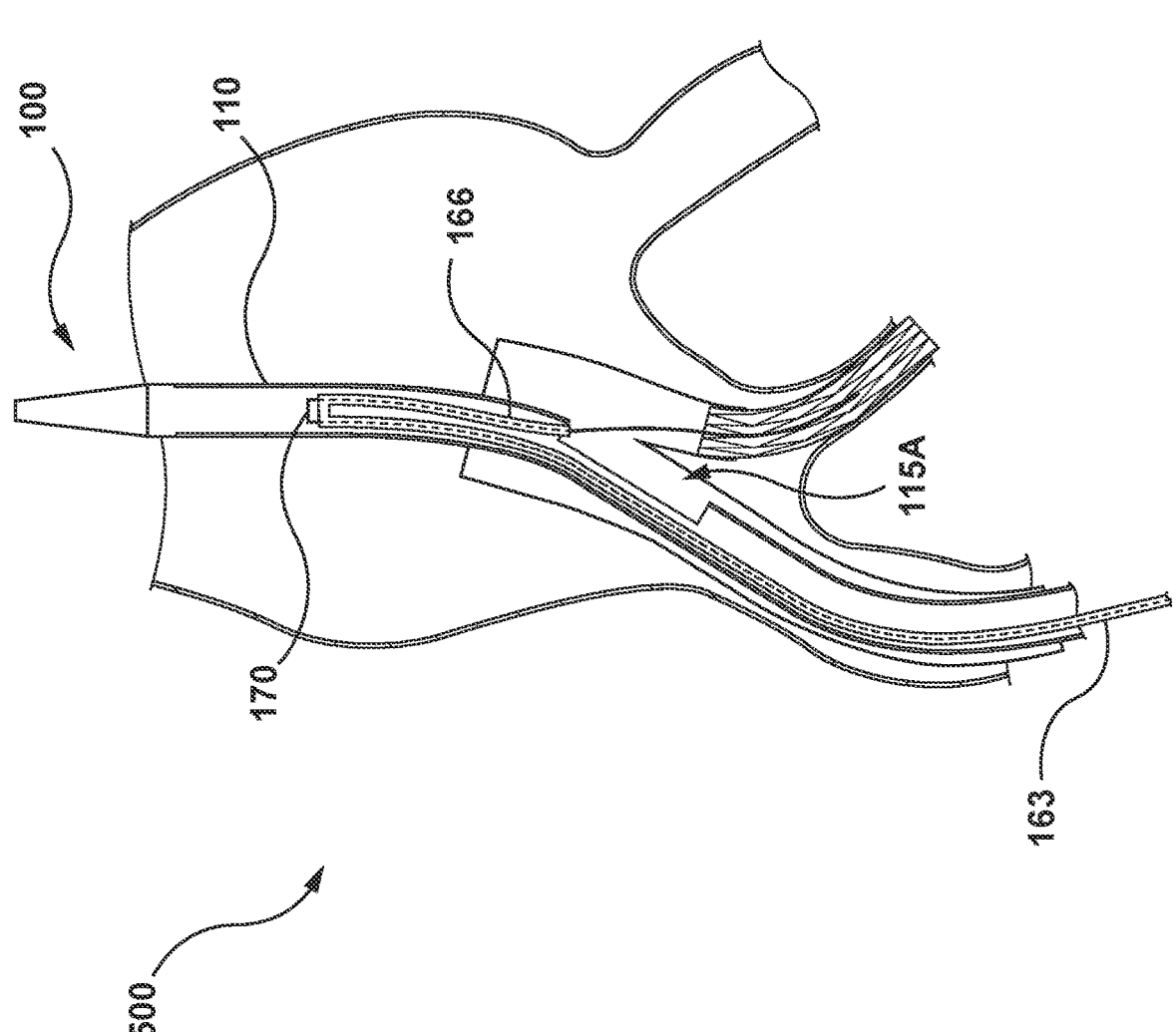
FIG. 17 shows a step in the method of FIG. 10, showing the delivery device being retracted from the internal iliac artery of the patient according to embodiments hereof.
Figures 18A, 18B:
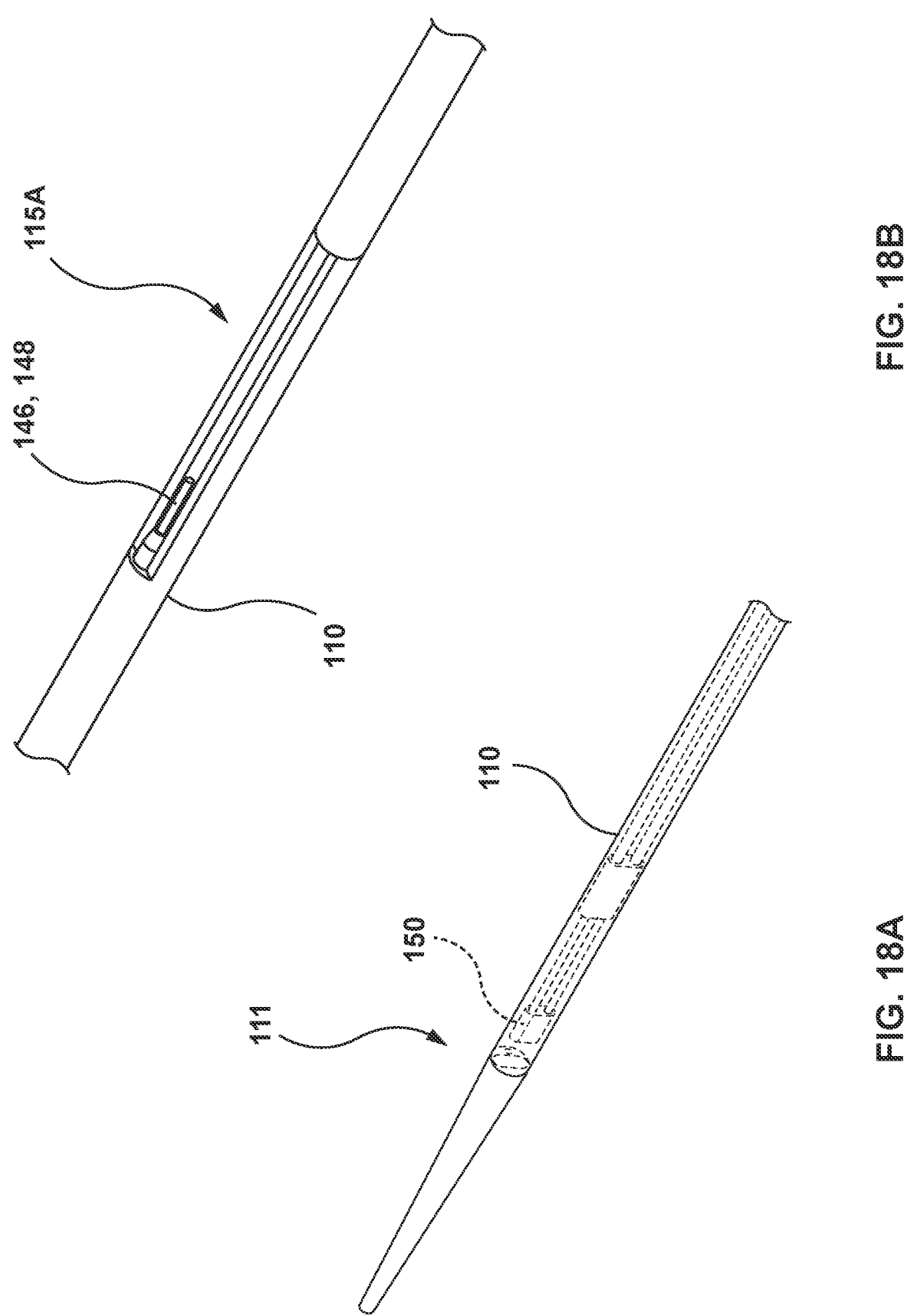
FIG. 18A shows a close-up view of a distal end of the delivery system according to embodiments hereof.
FIG. 18B shows a close-up view of a proximal end of the delivery system according to embodiments hereof.
Figure 18C:
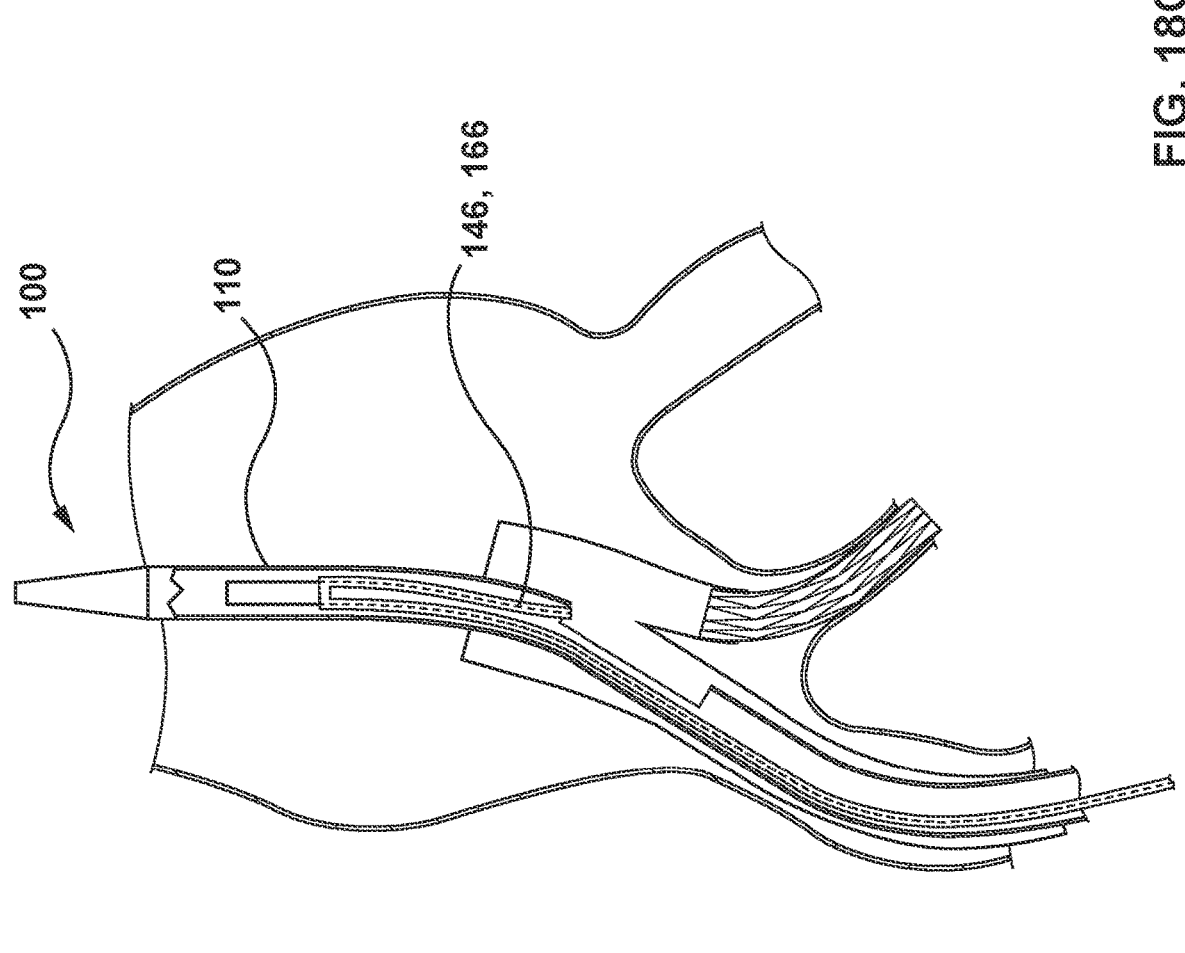
FIG. 18C shows a step in the method of FIG. 10, showing the stylet being retracted from the internal iliac artery of the patient according to embodiments hereof.

In a step 614 of the method 600, the internal iliac stent graft 200 is deployed at the desired location within the internal iliac artery 540 of the patient's vasculature 500, as shown in FIG. 16. In the embodiment shown, the internal iliac stent graft 200 is loaded on the balloon 190 that is coupled to the proximal end 168 of the second member 166 of the delivery device 160. To inflate the balloon, an inflation fluid is introduced to the delivery device 160 at the proximal end 165 of the first member 163 of the delivery device 160. The fluid is injected within first and second outer lumen portions 182A, 182B of the first member 163 at their proximal end, travels distally through the first and second outer lumen portions 182A, 182B of the first member 163 to the U-turn manifold 170 of the delivery device 160. When the inflation fluid reaches the U-turn manifold 170, the inflation fluid transfers to the second member 166 of the delivery device 160 via the first cut-out 179A of the first member 163, the opening 179 of the U-turn manifold 170, and the second cut-out 179B of the second member 166, as described previously with respect to FIGS. 8J-8K.

Thus, the inflation fluid travels distally through the first member 163 of the delivery device 160, flows through the opening 179 of the U-turn manifold 170, and flows into the first and second outer lumen portions 186A, 186B of the outer lumen 186 of the second member 166 of the delivery device 160. The inflation fluid then proximally through the first and second outer lumen portions 186A, 186B until the inflation fluid is between the distal and proximal ends 191, 192 of the balloon 190, where the inflation fluid exits the first and second outer lumen portions 186A, 186B through the first and second radial channels 197A, 197B and into the interior cavity 195 of the balloon 190, thereby inflating the balloon 190 to radially expand the internal iliac stent graft 200. This radial expansion deploys the internal iliac stent graft 200 within the internal iliac artery 540 of the patient. In most cases, a portion of the internal iliac stent 200 will overlap with a portion of the second branch 330 of the iliac branch device 300, as shown in FIG. 16. The inflation fluid may then be removed from the inflation lumens and the balloon 190 to deflate the balloon 190 for removal from the vasculature.

In a next step 616 of the method 600, the first member 163 of the delivery device 160 is pushed back distally into the first main lumen 114 of the shaft 110 of the delivery system 100, which pushes the U-turn manifold 170 of the delivery device 160 and the connector 150 of the stylet 140 distally, thereby pulling the second member 166 of the delivery device 160 and the second wire member 146 of the stylet 140 distally. In a next step 618, if necessary, the first wire member 143 may also be pushed distally to push the connector 150 distally, thereby pulling the second wire member 146 distally. Thus, the second member 163 of the delivery device and the second wire member 146 of the stylet 140 are moved distally back into the second main lumen 115 of the shaft 110.

Figures 19A, 19B:
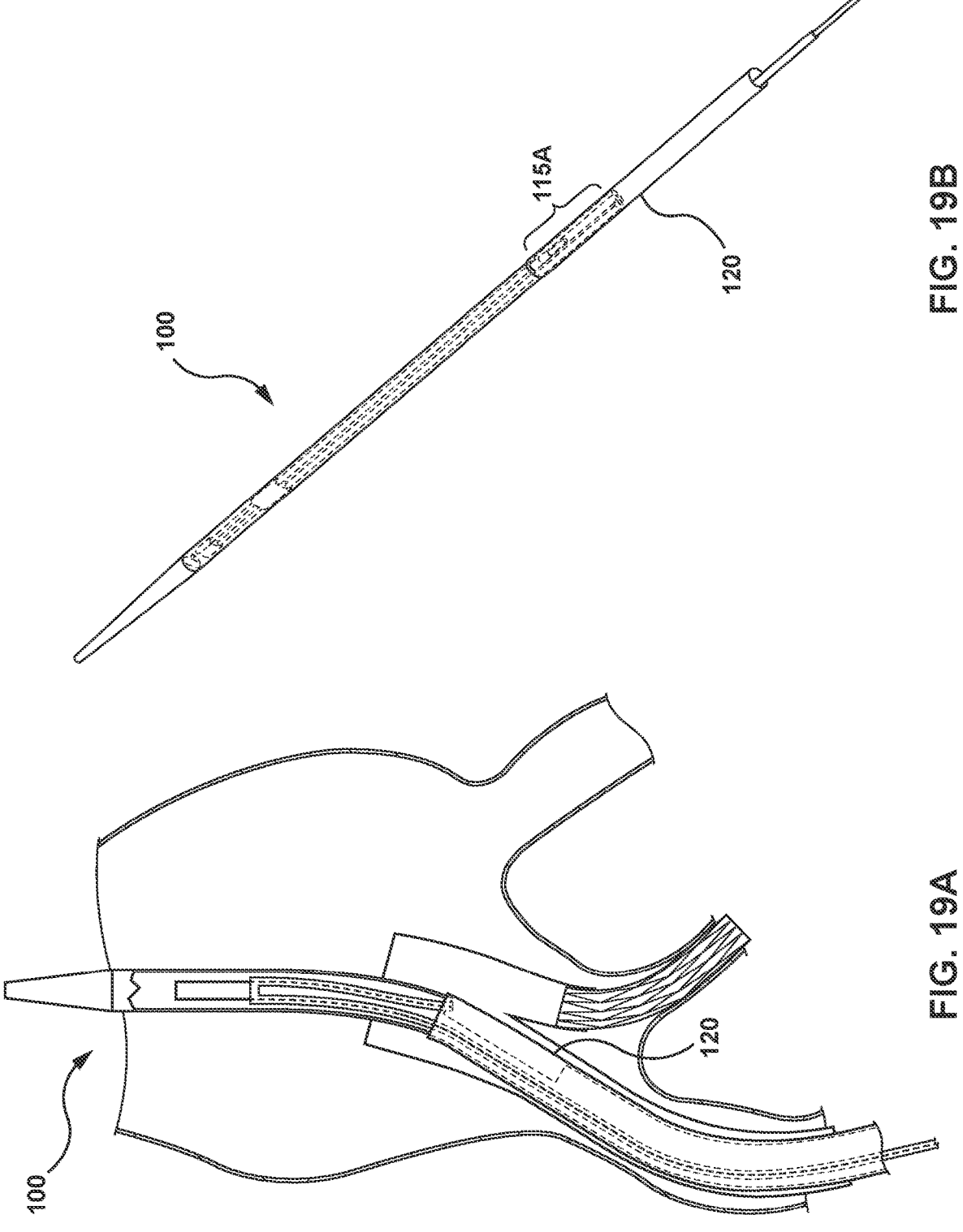
FIG. 19A shows a step in the method of FIG. 10, showing the cover being advanced distally over the skived portion of the shaft according to embodiments hereof.
FIG. 19B shows a perspective view of the delivery system according to embodiments hereof.

In a next step 620 of the method 600, the cover 120 of the delivery system 100 is advanced distally back over the skived portion 115A of the second main lumen 115 such that the skived portion 115A is covered or enclosed by the cover 120, returning the delivery system 100 to the covered configuration. The cover 120 of the delivery system 100 is advanced distally until the distal end 121 of the cover 120 aligns with the distal end of the skived portion 115A of the shaft 110 such that the skived portion 115A is entirely covered, as shown in FIGS. 19A-19B.

Figure 20:
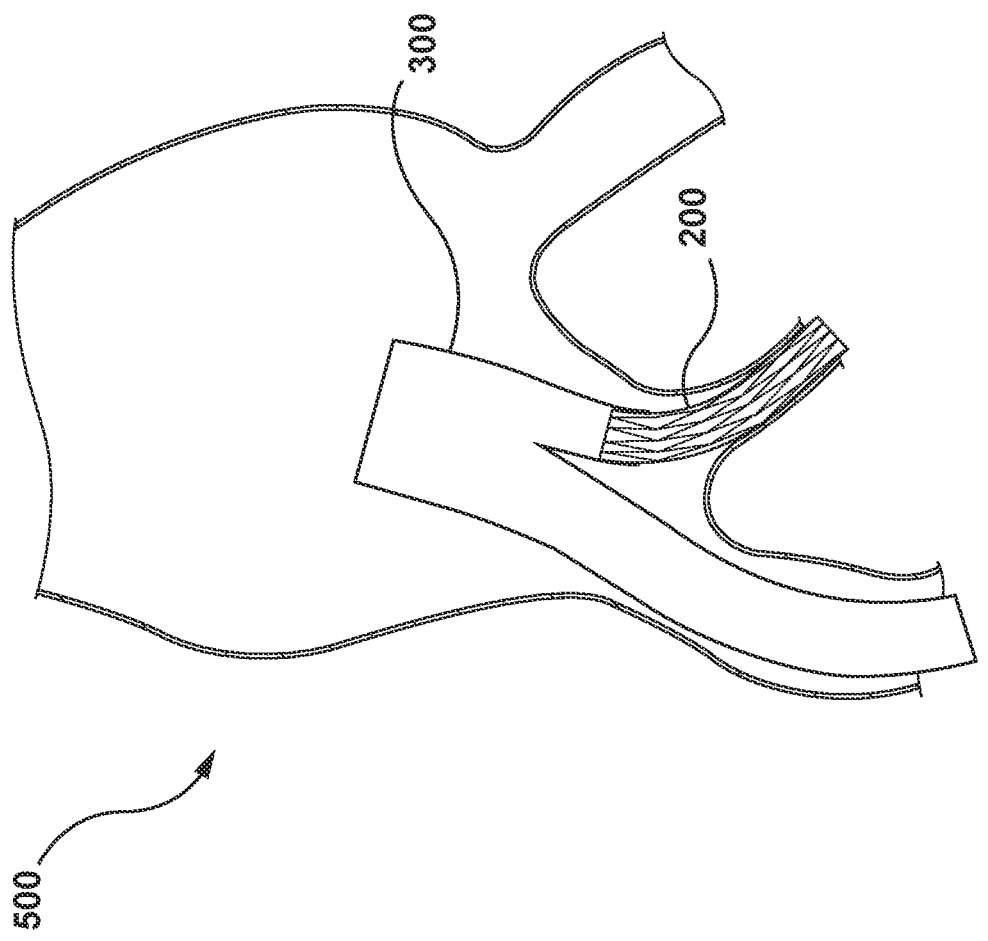
FIG. 20 shows a step in the method of FIG. 10, showing the delivery system being retracted from the vasculature of the patient according to embodiments hereof.

In a next step 622 of the method 600, the delivery system 100 is retracted proximally over the guidewire 400 until it is removed from the vasculature 500 of the patient, as shown in FIG. 20.

While the devices and methods have been disclosed herein as used for delivery of a stent graft into the internal iliac artery, they may be used for delivery of any catheter based device (e.g., stent graft, stent, balloon, etc.) and may be used in any suitable blood vessel. For example, the delivery system may be used in any situation in which it is beneficial to deliver a device in a retrograde manner, such as where a branch vessel extends at an acute angle relative to the delivery system.

It should be understood that various embodiments disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single device or component for purposes of clarity, it should be understood that the techniques of this disclosure may be performed by a combination of devices or components.

What is claimed is:

1. A delivery system comprising:
a shaft including a guidewire lumen, first main lumen, a second main lumen, wherein proximal portions of the first main lumen and the second main lumen are separated, and wherein distal portions of the first main lumen and the second main lumen form a common U-turn lumen; and
a delivery device including a first member disposed within the first main lumen of the shaft, a second member disposed within the second main lumen of the shaft, and a manifold coupling the first member and the second member, wherein the manifold is disposed within the common U-turn lumen of the shaft;
wherein proximal movement of the first member of the delivery device along a first longitudinal axis causes corresponding proximal movement of the manifold within the common U-turn lumen and corresponding proximal movement of the second member along a second longitudinal axis different from the first longitudinal axis.

2. The delivery system of claim 1 wherein the delivery device further includes a balloon coupled to the second member.

3. The delivery device of claim 2 wherein the first member includes a first central lumen and a first inflation lumen, the second member includes a second central lumen and a second inflation lumen, and the manifold fluidly couples the first inflation lumen and the second inflation lumen.

4. The delivery system of claim 3, further comprising a stylet including a first wire member disposed within the first main lumen of the delivery device, a second wire member disposed within the second main lumen of the delivery device, and a connector connecting distal ends of the first wire member and the second wire member, the connector being disposed within the common U-turn lumen of the shaft, wherein proximal movement of the first wire member causes corresponding proximal movement of the connector within the common U-turn lumen and corresponding proximal movement of the second wire member.

5. The delivery system of claim 1, further comprising a skived portion of the shaft, wherein the skived portion of the shaft exposes a portion of the second main lumen of the shaft.

6. The delivery system of claim 5, further comprising a cover extending from a proximal end of the delivery system to a distal portion of the delivery system, wherein the cover is movable relative to the shaft to cover and uncover the skived portion of the shaft.

7. The delivery system of claim 6, wherein the cover is longitudinally translatable to cover and uncover the skived portion of the shaft.

8. The delivery system of claim 1, further comprising a distal tip coupled to a distal end of the shaft, wherein the distal tip includes a tip guidewire lumen in communication with the guidewire lumen of the shaft.

9. The delivery system of claim 4, wherein the manifold of the delivery device includes a first lumen with the first member fixedly coupled therein, and second lumen with the second member fixedly coupled therein, and an opening between the first lumen and the second lumen.

10. The delivery system of claim 9, wherein the first member includes a first opening aligned with the first inflation lumen and the opening of the manifold and the second member includes a second opening aligned with the second inflation lumen of the opening, wherein inflation fluid injected into the first inflation lumen is configured to move distally within the first inflation lumen, exit the first inflation lumen via the first opening, move through the opening in the manifold and into the second inflation lumen through the second opening, and move proximally through the second inflation lumen to the balloon of the delivery device.

11. The delivery system of claim 9, wherein the first wire member of the stylet extends through the first lumen of the manifold and the second wire member of the stylet extends through the second lumen of the manifold.

* * * * *